(12) United States Patent
Moss et al.

(10) Patent No.: US 12,070,446 B2
(45) Date of Patent: *Aug. 27, 2024

(54) STANDARDIZED PSYCHOACTIVE ALKALOID EXTRACT COMPOSITION

(71) Applicant: Psilo Scientific Ltd., Burnaby (CA)

(72) Inventors: Ryan Moss, Vancouver (CA); Benjamin Lightburn, West Vancouver (CA); Lisa Ranken, Lake Country (CA)

(73) Assignee: Psilo Scientific, Ltd., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/514,982

(22) Filed: Nov. 20, 2023

(65) Prior Publication Data

US 2024/0082216 A1    Mar. 14, 2024

Related U.S. Application Data

(63) Continuation of application No. 18/238,478, filed on Aug. 26, 2023, now Pat. No. 11,957,659, which is a continuation of application No. 17/840,482, filed on Jun. 14, 2022, now Pat. No. 11,786,506, which is a continuation of application No. PCT/CA2021/051701, filed on Nov. 29, 2021.

(60) Provisional application No. 63/131,028, filed on Dec. 28, 2020, provisional application No. 63/139,453, filed on Jan. 20, 2021.

(30) Foreign Application Priority Data

Mar. 24, 2021   (CA) ........................... 3113240
Jul. 1, 2021   (CA) ........................... 3123774
Nov. 29, 2021   (WO) ............... PCT/CA2021/051702
Dec. 22, 2021   (WO) ............... PCT/CA2021/051876
Dec. 27, 2021   (WO) ............... PCT/CA2021/051891

(51) Int. Cl.

| A61K 31/4045 | (2006.01) |
|---|---|
| A61K 9/00 | (2006.01) |
| A61K 9/08 | (2006.01) |
| A61K 9/20 | (2006.01) |
| A61K 9/70 | (2006.01) |
| A61K 31/355 | (2006.01) |
| A61K 31/375 | (2006.01) |
| A61K 31/405 | (2006.01) |
| A61K 31/675 | (2006.01) |
| A61K 36/07 | (2006.01) |
| A61K 45/06 | (2006.01) |
| A61K 47/10 | (2017.01) |
| A61K 47/12 | (2006.01) |

(52) U.S. Cl.
CPC ........ *A61K 31/4045* (2013.01); *A61K 9/0053* (2013.01); *A61K 9/0078* (2013.01); *A61K 9/08* (2013.01); *A61K 9/2095* (2013.01); *A61K 9/7023* (2013.01); *A61K 31/355* (2013.01); *A61K 31/375* (2013.01); *A61K 31/405* (2013.01); *A61K 31/675* (2013.01); *A61K 36/07* (2013.01); *A61K 45/06* (2013.01); *A61K 47/10* (2013.01); *A61K 47/12* (2013.01); *A61K 2236/15* (2013.01); *A61K 2236/17* (2013.01); *A61K 2236/39* (2013.01); *A61K 2236/53* (2013.01)

(58) Field of Classification Search
CPC .................. A61K 9/00; A61K 2236/00; A61K 2236/4045; A61K 2236/05; A61K 31/4045; A61K 9/0053; A61K 9/0078; A61K 9/08; A61K 9/2095; A61K 31/355; A61K 31/375; A61K 31/405; A61K 31/675; A61K 36/07; A61K 45/06; A61K 47/10; A61K 47/12; A61K 2236/15; A61K 2236/17; A61K 2236/39; A61K 2236/53
See application file for complete search history.

(56) References Cited

U.S. PATENT DOCUMENTS

| 3,183,172 A | 5/1965 | Roger et al. |
|---|---|---|
| 5,550,166 A | 8/1996 | Ostlund et al. |
| 8,846,075 B2 | 9/2014 | Jonsson et al. |
| 9,308,175 B2 | 4/2016 | Pellikaan et al. |

(Continued)

FOREIGN PATENT DOCUMENTS

| CA | 2339353 A1 | 4/2000 |
|---|---|---|
| CA | 2794734 A1 | 10/2011 |

(Continued)

OTHER PUBLICATIONS

Final Office Action in U.S. Appl. No. 17/351,149, dated Jan. 24, 2022, 11 Pages.

(Continued)

*Primary Examiner* — Aaron J Kosar
(74) *Attorney, Agent, or Firm* — Mintz, Levin, Cohn, Ferris, Glovsky and Popeo, P.C.

(57) ABSTRACT

A transmucosal psychoactive alkaloid composition including a psychoactive alkaloid extract or synthetic psychoactive alkaloid. The alkaloids in the extract are predominantly dephosphorylated rather than phosphorylated. The transmucosal psychoactive alkaloid composition also includes a mucoadhesive polymer, a carrier, and optional further excipients. The non-ingestive composition may be taken orally through the mucosa. A process for obtaining an oral transmucosal psychoactive alkaloid composition includes dephosphorylating the alkaloid during extraction, purifying the extracted alkaloid and standardizing to a specific concentration by adding measured quantities of excipients.

30 Claims, 6 Drawing Sheets

(56) References Cited

U.S. PATENT DOCUMENTS

| | | | |
|---|---|---|---|
| 11,298,388 | B2 | 4/2022 | Lightburn et al. |
| 11,331,357 | B2 | 5/2022 | Lightburn et al. |
| 11,382,942 | B2 | 7/2022 | Lightburn et al. |
| 11,786,506 | B2 | 10/2023 | Moss et al. |
| 2017/0157343 | A1 | 6/2017 | Davidson et al. |
| 2018/0021326 | A1 | 1/2018 | Stamets |
| 2019/0142851 | A1 | 5/2019 | Chadeayne |
| 2020/0375967 | A1 | 12/2020 | Stamets |
| 2022/0054402 | A1 | 2/2022 | Kaufman |
| 2022/0331292 | A1 | 10/2022 | Maurice |
| 2022/0409584 | A1 | 12/2022 | Bilal et al. |

FOREIGN PATENT DOCUMENTS

| | | |
|---|---|---|
| CA | 3050679 A1 | 7/2018 |
| CA | 3052974 A1 | 8/2018 |
| CA | 3078765 A1 | 4/2019 |
| CA | 3088384 A1 | 10/2020 |
| CA | 3137106 A1 | 10/2020 |
| CA | 3097246 A1 | 11/2021 |
| CN | 101292727 A | 10/2008 |
| CN | 101491647 A | 7/2009 |
| DE | 264023 A1 | 1/1989 |
| GB | 911946 A | 12/1962 |
| WO | 03074526 A2 | 9/2003 |
| WO | 2016161138 A1 | 10/2016 |
| WO | 2019073379 A1 | 4/2019 |
| WO | 2020157569 A1 | 8/2020 |
| WO | 2020181194 A1 | 9/2020 |
| WO | 2021003467 A1 | 1/2021 |
| WO | 2021007152 A1 | 1/2021 |

OTHER PUBLICATIONS

2011) Guidance on Equivalence of Herbal Extracts in Complementary Medicines, Therapeutic Goods Administration, 1:16 pages.
International Search Report and Written Opinion for PCT/CA2021/051495, mailed on Jan. 26, 2022, 11 pages.
International Search Report and Written Opinion received for PCT Application No. PCT/CA2021/051702, mailed on Mar. 2, 2022, 11 pages.
International Search Report and Written Opinion received for PCT Application No. PCT/CA2021/050813, mailed on Sep. 9, 2021, 7 Pages.
International Search Report and Written Opinion received for PCT Application No. PCT/CA2021/050822, mailed on Oct. 19, 2021, 12 Pages.
International Search Report and Written Opinion received for PCT Application No. PCT/CA2021/050823, mailed on Sep. 20, 2021, 12 Pages.
International Search Report and Written Opinion received for PCT Application No. PCT/CA2021/051701, mailed on Feb. 1, 2022, 22 Pages.
International Search Report and Written Opinion received for PCT Application No. PCT/CA2021/051876, mailed on Mar. 29, 2022, 9 Pages.
International Search Report and Written Opinion received for PCT Application No. PCT/CA2021/051891, mailed on Feb. 28, 2022, 6 Pages.
2017) Mikey's Psilly Ethanol Extract, Available on: https://mycotopia.net/topic/100561-mikeys-psilly-ethanol-exract/, 13 pages.
Non-Final Office Action in U.S. Appl. No. 17/348,697, dated Dec. 13, 2021, 6 pages.
Non-Final Office Action in U.S. Appl. No. 17/351,149, dated Oct. 13, 2021., 10 pages.
Non-Final Office Action in U.S. Appl. No. 17/483,601, dated Dec. 13, 2021, 6 pages.
Non-Final Office Action in U.S. Appl. No. 17/697,798, dated Sep. 2, 2022, 8 pages.
Notice of Allowance in U.S. Appl. No. 17/348,697, dated Feb. 7, 2022, 10 pages.
Notice of Allowance in U.S. Appl. No. 17/348,697, dated Mar. 22, 2022, 9 pages.
Notice of Allowance in U.S. Appl. No. 17/351,149, dated Mar. 21, 2022, 7 pages.
Notice of Allowance in U.S. Appl. No. 17/351,149, dated Apr. 29, 2022, 8 pages.
Notice of Allowance in U.S. Appl. No. 17/483,601, dated Feb. 4, 2022, 8 pages.
Notice of Allowance in U.S. Appl. No. 17/483,601, dated Feb. 25, 2022, 9 pages.
2017) Truffle Magic—Simple Method of Psilocybin Extraction.
U.S. Appl. No. 17/840,502 Non-Final Office Action, dated Mar. 2, 2023, 10 pages.
U.S. Appl. No. 17/841,323 Non-Final Office Action, dated Apr. 13, 2023, 12 pages.
Adejoke et al. (2019) "A review on classes, extraction, purification and pharmaceutical importance of plants alkaloid", Journal of Medicinal and Chemical Sciences, 2:130-139.
Anastos et al. (Jan. 2006) "The determination of psilocin and psilocybin in hallucinogenic mushrooms by HPLC utilizing a dual reagent acidic potassium permanganate and tris(2,2'-bipyridyl)ruthenium(II) chemiluminescence detection system", Journal of Forensic Sciences, 51(1):45-51.
Bauer Rudolf (1998) "Quality Criteria and Standardization of Phytopharmaceuticals: Can Acceptable Drug Standards be Achieved?", Drug Information Journal, 32(1):101-110.
Beug et al. (1981) "Quantitative Analysis of Psilocybin and Psilocin in Psilocybe Baeocystis (Singer and Smith) by High-performance Liquid Chromatography and by Thin-layer Chromatography", Journal of Chromatography A, 207(3):379-385.
Casale J. F. (Jan. 1985) "An Aqueous-Organic Extraction Method for the Isolation and Identification of Psilocin from Hallucinogenic Mushrooms", Journal of Forensic Sciences, 30(1):247-250.
Choudhary et al. (Dec. 6, 2011) "An Overview of Advances in the Standardization of Herbal Drugs", Indian Journal of Pharmaceutical Education and Research, 2(2):55-70.
De Boer P (Jun. 24, 2017) "Simple Method of Psilocybin Extraction", Blog: Fresh Trujjles and Grow kits.
Fakhari et al. (Jul. 2010) "Optimized Ultrasound-assisted Extraction procedure for The Analysis of Opium Alkaloids In Papaver Plants by Cyclodextrin-modified Capillary Electrophoresis", Journal of Separation Science, 33(14):2153-2159.
Fricke et al. (2019) "Production Options for Psilocybin: Making of the Magic", Chemistry, 25(4):897-903.
Gartz J (1994) "Extraction and analysis of indole derivatives from fungal biomass", Journal of Basic Microbiology, 34(1):17-22.
Kunle et al. (Mar. 2012) "Standardization of herbal medicines—a review", International Journal of Biodiversity and Conservation, 4(3):101-112.
Kysilka et al. (Jun. 1990) "A Novel Extraction Procedure for Psilocybin and Psilocin Determination in Mushroom Samples", Planta Medica, 56(3):327-328.
Kysilka R. (1990) "Chromatographic determination of psilocybin and psilocin in fruit bodies and mycelia of hallucinogenic mushrooms", Chem Listy, 84:988-992.
Lenz et al. (Jan. 20, 2020) "Injury-Triggered Blueing Reactions of Psilocybe "Magic" Mushrooms", Angewandte Chemie, 59(4):1450-1454.
Mahmoudi et al. (2018) "Alteration of depressive-like behaviors by psilocybe cubensis alkaloid extract in mice: The role of glutamate pathway", Research Journal of Pharmacognosy, 5(2):17-24.
Moldavan et al. (2001) "The effect of Psilocybe cubensis extract on hippocampal neurons in vitro", Fiziologichnyi Zhurnal, 47(6):15-23.
Ojha et al. (2017) "Recent advancement in emu Igel: A novel approach for topical drug delivery", International Journal of Advances in Pharmacy and Biotechnology, 6(1):17-23.
Ong Eng S. (2004) "Extraction Methods and Chemical Standardization of Botanicals and Herbal Preparations", Journal of Chromatography B, 812(1-2):23-33.

(56) References Cited

OTHER PUBLICATIONS

Passie et al. (2002) "The pharmacology of psilocybin", Addiction biology, 7(4):357-364.

Pellegrini et al. (2013) "Magic Truffles or Philosopher's Stones: a Legal Way to Sell Psilocybin?", Drug Testing and Analysis, 5(3):182-185.

Perkal et al. (Aug. 1, 1980) "Determination of hallucinogenic components of Psilocybe mushrooms using high-performance liquid chromatography", Journal of Chromatography A, 196(1):180-184.

Poliwoda et al. (Sep. 2014) "Determination of muscimol and ibotenic acid in mushrooms of Amanitaceae by capillary electrophoresis", Electrophoresis, 35(18):2593- 599.

Psilocybin Expert (Feb. 13, 2018) "Formulating New 'Magic Mushroom' Compositions", Psilocybin Technology.

Roderick (Dec. 29, 2019) "Psilocybin and Cannabis Cocktails", Psillow, 9 Pages.

Roderick (2019) "Psilocybin Tincture", 2 pages.

Stebelska Katarzyna (2016) "Assays for Detection of Fungal Hallucinogens Such as Psilocybin and Psilocin", 84:909-926.

Therapeutics Goods Administration (TGA) "Guidance on Equivalence of Herbal Extracts in Complementary Medicines." Aus. Govt. TGA, Dept of Health and Ageing. Feb. 2011 v 1.0, 16 pages (Year: 2011).

Tsujikawa et al. (2003) "Morphological and Chemical Analysis of Magic Mushrooms in Japan", Forensic Sci Int., 138(1-3):85-90.

Tuan et al. (2019) "Optimization of Spray Drying Condition from Trametes Versicolor Mushroom Extract", Journal of Science and Technology, 39A:25-30.

Jul. 17, 2003) Chemistry MDMA hiveboard, 9 Pages.

Wieczorek et al. (2015) "Bioactive Alkaloids of Hallucinogenic Mushrooms", Studies in Natural Products Chemistry, 46:133-168.

Zhang et al. (Dec. 2007) "Macroporous Resin Adsorption for Purification of Flavonoids in Houttuynia cordata Thunb", Chinese Journal of Chemical Engineering, 15(6):872-876.

Zhang et al. (2018) "Techniques for Extraction and Isolation of Natural Products: a Comprehensive Review", 13(20):26 pages.

Zhuk et al. (Mar. 27, 2015) "Research on acute toxicity and the behavioral effects of methanolic extract from psilocybin mushrooms and psilocin in mice", Toxins (Basel), 7(4):1018-1029.

STANDARDIZED PSYCHOACTIVE ALKALOID EXTRACT COMPOSITION

This application is a continuation of U.S. application Ser. No. 18/238,478 filed on Aug. 26, 2023, which is a continuation of U.S. application Ser. No. 17/840,482, which is a continuation of International Application No. CA/2021/051701 filed Nov. 29, 2021, which claims the benefit of Canadian Application No. 3113240 filed Mar. 24, 2021, U.S. Provisional Patent Application No. 63/131,028 filed on Dec. 28, 2020, and U.S. Provisional Patent Application No. 63/139,453 filed on Jan. 20, 2021. This application also claims priority to Canadian Application No. 3123774 filed Jul. 1, 2021, International Application No. PCT/CA2021/051876 filed Dec. 22, 2021, International Application No. PCT/CA2021/051702 filed Nov. 29, 2021, and International Application No. PCT/CA2021/051891 filed Dec. 28, 2021, each of which are incorporated by reference in their entireties.

TECHNICAL FIELD

This application relates to a transmucosal composition. More specifically, the present invention relates to a non-ingestive transmucosal composition of psychoactive alkaloids. The present invention also relates to a process for preparing the non-ingestive transmucosal composition.

BACKGROUND

A psychoactive substance is a chemical substance that changes brain function and results in alterations in perception, mood, consciousness, cognition, or behavior. The psychoactivity of these substances may include sedative, stimulant, euphoric, deliriant, and hallucinogenic effects. These substances have been used recreationally, to purposefully improve performance or alter one's consciousness, and as entheogens for ritual, spiritual, or shamanic purposes. Some categories of psychoactive compounds have also shown therapeutic values and are prescribed by physicians and other healthcare practitioners.

The active constituents of the majority of psychoactive plants, fungi, animals, or yeasts fall within a class of basic, naturally occurring, nitrogen-containing, organic compounds called alkaloids (e.g. nicotine, morphine, cocaine, mescaline, caffeine, ephedrine, psilocin). Alkaloids have a wide range of pharmacological activities including antimalarial, antiasthma, anticancer, cholinomimetic, vasodilatory, antiarrhythmic, analgesic, antibacterial, and antihyperglycemic activities. Many alkaloids have found use in traditional or modern medicine, or as starting points for drug discovery. Recently, psychotropic and stimulant activities of psychoactive alkaloids have been gaining interest from researchers as therapeutic agents for treating various conditions such as alcoholism, opioid addiction and pain to name a few.

Psychoactive alkaloids present in natural sources can be broadly divided into two categories, which are phosphorylated psychoactive alkaloids and dephosphorylated psychoactive alkaloids, although other non-phosphorylatable psychoactive alkaloids may also be present in a natural source. Phosphorylated psychoactive alkaloids are phosphoric acid esters of dephosphorylated psychoactive alkaloids and are biosynthesized in natural sources. Dephosphorylated forms of these psychoactive alkaloids are the bioactive forms that are converted through phosphatase action or chemical hydrolysis. In the human body, upon ingestion, phosphorylated psychoactive alkaloids are dephosphorylated to their corresponding dephosphorylated bioactive forms upon the action of endogenous phosphatase enzymes, which are predominantly found in the gut. For example, to achieve its desired effect, psilocybin must be dephosphorylated to psilocin by a phosphatase enzyme in the gastrointestinal tract.

Oral administration of phosphorylated psychoactive alkaloid compositions via the human gastrointestinal tract allows the conversion of the phosphorylated form to the corresponding biological effective dephosphorylated form. Additionally, the oral route of administration is convenient and ensures patient compliance. However, bioavailability of active pharmaceutical ingredients (APIs) via enteric administration is heavily dependent on an ingredient's ability to be absorbed across the intestinal epithelium and first pass metabolism. Enteric routes of administration also pose challenges such as long onset of action, gastric irritation, etc. Further, the ingestion of dosage forms via the oral route, which involves chewing or swallowing, is problematic for children and geriatric patients.

Often, to overcome these challenges, administration of an API is done via parenteral and topical routes. Delivery of APIs via these routes of administration allows bypassing the first pass metabolism. Furthermore, onset of action of the API is faster than oral ingestion. Dosage forms for administration of psychoactive alkaloids via parenteral routes, such as nasal sprays, inhalers, sublingual absorption, and like have been considered by researchers.

The non-ingestive, oral transmucosal route of administration is an oral non-enteric drug delivery method, which allows bypassing the first pass metabolism, and circumvents gastric irritation, if any. Further, since transmucosal membranes have a rich blood supply and are permeable, this route of administration results in rapid delivery of an API into systemic circulation.

U.S. Pat. No. 9,308,175B2 to Pellikaan relates to a pharmaceutical dosage unit for sublingual, buccal, pulmonary or oral administration. The dosage form contains one or more water-insoluble pharmaceutically active substances, i.e. cannabinoids.

U.S. Pat. No. 8,846,075B2 to Jonsson describes a composition material for transmucosal delivery. The composition has at least one anionic natural polymeric carbohydrate selected from alginate and xanthan gum, having at least one biologically active substance ionically bound thereto, and one wettable, insoluble polymeric carbohydrate. Suitable example of said at least one biologically active substance includes alkaloids.

PCT/US2020/040826 to Arnold discloses parenteral methods of delivering psilocin and psilocybin, without distinguishing between the two, via parenteral methods.

However, parenteral routes of administration do not facilitate the dephosphorylation of phosphorylated psychoactive alkaloids because they are delivered to an area of the body where little to no dephosphorylation occurs. Thus, often only little to none of the corresponding bioactive dephosphorylated psychoactive alkaloids are delivered to the intended site of action.

Additionally, psychoactive alkaloid extracts are often present in form of a sticky tar, which is difficult to handle or standardize into compositions with specific amounts of psychoactive alkaloids that can be formulated into desired dosage forms.

This background information is provided to reveal information believed by the applicant to be of possible relevance to the present invention. No admission is necessarily intended, nor should be construed, that any of the preceding information constitutes prior art against the present invention.

SUMMARY OF INVENTION

The inventors have realized that there is a need for a non-ingestive psychoactive alkaloid composition capable of providing desired levels of bioactivity in the systemic circulation. In particular, there is need for a non-ingestive psychoactive alkaloid composition which allows for rapid delivery of the psychoactive alkaloid into the systemic circulation, and does not adversely affect the bioavailability of the psychoactive alkaloid, thus allowing the psychoactive alkaloid to achieve the desired psychoactive effects. The psychoactive alkaloid composition is an oral transmucosal composition with a dephosphorylated psychoactive alkaloid extract, a mucoadhesive polymer, a carrier, and optionally one or more further excipients. The psychoactive alkaloids may be extracted or synthetic.

Disclosed is a transmucosal psychoactive alkaloid composition comprising: 1-40% by weight of a psychoactive alkaloid extract that comprises more dephosphorylated psychoactive alkaloid than phosphorylated psychoactive alkaloid; 1-50% of mucoadhesive polymer; and 10-65% carrier.

Also disclosed is a transmucosal psychoactive alkaloid composition comprising: 1-40% by weight of a synthetic dephosphorylated psychoactive alkaloid; 1-50% of mucoadhesive polymer; and 10-65% carrier.

Further disclosed is a process for obtaining a transmucosal psychoactive alkaloid composition, the process comprising: extracting a psychoactive alkaloid from a dried powdered psychoactive alkaloid source using an acidified solvent with a pH lower than 3.5, to obtain a psychoactive alkaloid liquid; adjusting the pH of the psychoactive alkaloid liquid to a pH ranging from 3.5-4.5; evaporating the solvent from the psychoactive alkaloid liquid to obtain a psychoactive alkaloid extract with more dephosphorylated psychoactive alkaloid than phosphorylated psychoactive alkaloid; and mixing the psychoactive alkaloid extract with a mucoadhesive polymer and a carrier to obtain the oral transmucosal psychoactive alkaloid composition.

This summary does not necessarily describe all features of the invention in detail and is not intended to limit the invention.

BRIEF DESCRIPTION OF DRAWINGS

The following drawings illustrate embodiments of the invention, which should not be construed as restricting the scope of the invention in any way.

DESCRIPTION

A. Glossary

Figure 1:
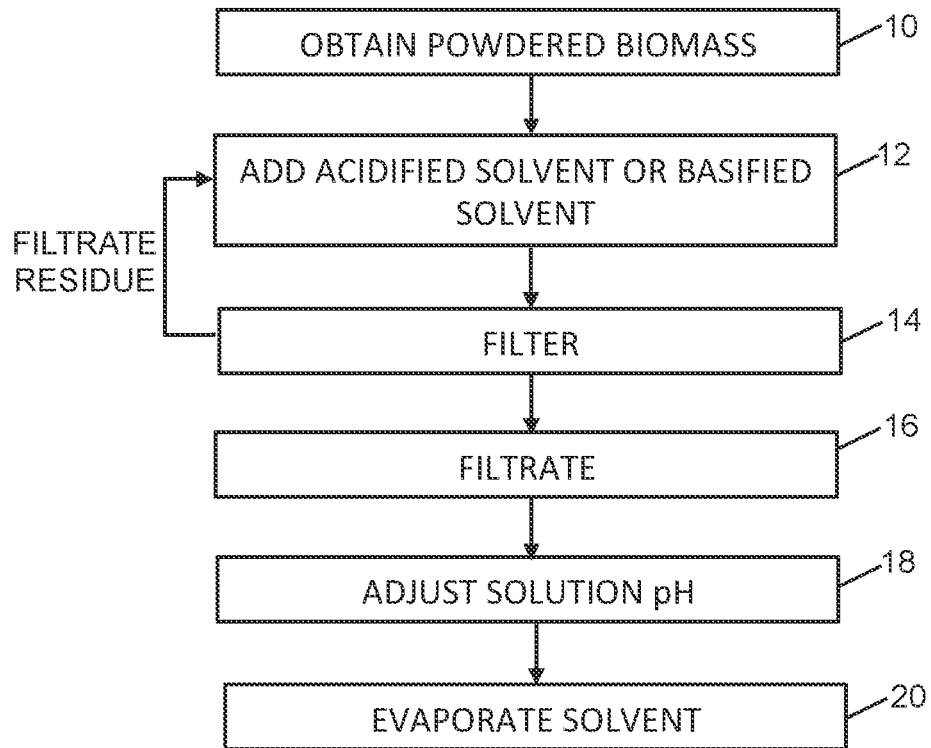
FIG. 1 illustrates the steps of a process for obtaining a psychoactive alkaloid extract with dephosphorylation control, according to an embodiment of the present invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," and the like include the number recited, and any tolerance explicitly or implicitly associated with it, and refer to ranges which can be subsequently broken down into subranges as discussed above. Finally, as will be understood by one skilled in the art, a range includes each individual member.

The term "psychoactive alkaloid" used herein refers to alkaloids that upon ingestion or other bodily intake are capable of changing brain function, for example resulting in alterations in perception, mood, consciousness, cognition, or behavior. The psychoactive alkaloid to which the present invention applies is predominantly a dephosphorylated psychoactive alkaloid, rather than a phosphorylated alkaloid or non-phosphorylatable alkaloid.

The term "psychoactive alkaloid source" used herein refers to a fungus, a mycelium, a spore, a plant, a bacterium, an animal or a yeast, which has in it a phosphorylated psychoactive alkaloid, a dephosphorylated psychoactive alkaloid, or a combination or both. The source of the psychoactive alkaloid can also be an extract or a solution with a phosphorylated psychoactive alkaloid, a dephosphorylated psychoactive alkaloid, or a combination of both.

The term "phosphorylatable" refers to psychoactive alkaloids that have phosphorylated derivatives and includes psychoactive alkaloids in both their phosphorylated and dephosphorylated forms.

The term "psychoactive alkaloid composition" used herein can also be referred to as "composition" and describes a mixture of a psychoactive alkaloid, a mucoadhesive polymer, a carrier, and optionally one or more excipients. The composition can be of pharmaceutical, nutraceutical, or veterinary grade.

The term "psychoactive alkaloid liquid" used herein refers to psychoactive alkaloid obtained in liquid form after a dried powdered biomass of a psychoactive alkaloid source has been extracted using an acidified solvent or a basified solvent. The liquid form can be a solution or a slurry.

The term "purified psychoactive alkaloid solution" refers to a solution of one or more desired psychoactive alkaloids, where the solution is free of impurities or contains fewer impurities compared to a similar psychoactive alkaloid solution that has not undergone any purification. The purified solution is obtained after a psychoactive alkaloid extracted from its source has been purified using a resinous material as described herein. Complete or partial evaporation of solvent from the purified psychoactive alkaloid solution results in a purified psychoactive alkaloid extract.

The term "psychoactive alkaloid extract" used herein refers to a psychoactive alkaloid extract obtained by an extraction process described herein or other process. The extract can be in a powdered or a semi-solid or slurry form.

The term "purified psychoactive alkaloid extract" used herein refers to a psychoactive alkaloid extract which has been purified using resinous material as described herein or otherwise. The purified psychoactive alkaloid extract has fewer impurities compared to a similar psychoactive alkaloid extract that has not undergone any purification. The extract can be in a powdered or a semi-solid or slurry form.

As used herein, the expression "standardization of" or "standardizing" the psychoactive alkaloid extract refers to adding a measured amount of a mucoadhesive polymer, a carrier, and optionally one or more further excipients to a psychoactive alkaloid extract to achieve an oral transmucosal psychoactive alkaloid composition. Addition of a pre-calculated percentage concentration of non-active pharmaceutical ingredients to the psychoactive alkaloid extract results in standardization of the oral transmucosal psychoactive alkaloid composition. The standardization process ensures that the oral transmucosal psychoactive alkaloid composition has a specific amount of total psychoactive alkaloid content in the composition. This specific amount is accurate up to two or three significant figures. This specific amount is defined as a percentage by weight and can be selected by a person of skill in the art according to preference.

The term "resin" as used herein is intended to refer to a solid or highly viscous substance of plant, mineral, or synthetic origin that has been typically converted into a polymer. Resins are usually mixtures of organic compounds. They are typically used in chromatographic techniques as a stationary phase to purify and separate compounds depending on their polarity. Resins can be physically or chemically modified to provide specificity to bind or repel particular molecules within sometimes very complex mixtures.

As used herein, the term "ion exchange resin" refers to an insoluble organic polymer containing charged groups that attract and hold oppositely charged ions present in a surrounding solution in exchange for counterions previously held. Suitable ion exchange resins to be used herein contain cationic groups that attract and hold anions present in a surrounding solution and are sometimes referred to as "anion ion-exchange resins". Similarly, other ion exchange resins used herein contain anionic groups that attract and hold cations present in a surrounding solution and are sometimes referred to as "cation ion-exchange resins".

The term "macroporous resin" as used herein refers to a nonionic, cation or anion resin with very small, highly cross-linked polymer particles with tiny channels. Macroporous resins are generally used for the adsorption of organic constituents due to their hydrophobic properties and are thus used to separate and purify compounds. The adsorption capacity of macroporous resins not only correlates with the physical and chemical properties of the adsorbent, but also with the size and chemical features of the adsorbed substance.

The term "adsorbed psychoactive alkaloid" refers to one or more alkaloids that are adsorbed onto a resinous material.

The term "purified water" includes deionized water, distilled water, reverse osmosis water, or otherwise purified water which is substantially without free ions.

As used herein, the term "specific amount" when referring to a total psychoactive alkaloid content means a desired percentage, accurate to one or two decimal places or one, two or three significant figures, of total psychoactive alkaloid content in a psychoactive alkaloid composition or a psychoactive alkaloid extract. The specific amount is defined as a percentage by weight and can be selected by a person of skill in the art according to preference.

The term "specific pH" herein refers to a definite pH value of a solvent or a psychoactive alkaloid liquid obtained by adding an acidified solvent or a basified solvent.

The term "desired amount" herein refers to an amount of a phosphorylated psychoactive alkaloid or a dephosphorylated psychoactive alkaloid in a total psychoactive alkaloid content, in the psychoactive alkaloid liquid, extract or composition. The amount of each of these alkaloids is controlled by the process for making the psychoactive alkaloid extract or psychoactive alkaloid composition. The amounts can be altered by a person of skill in the art according to preference. The amounts are usually percentages by weight that may be accurate up to two or three significant figures.

The "impurities" herein are commonly undesired, but not necessarily harmful, substances encountered while extracting psychoactive alkaloids from a natural source. Impurities may include sugars, carbohydrates, chitin, chitosan, fats, minerals, waxes, and/or proteins. The impurities being removed from a psychoactive alkaloid extract will vary depending on the source of the psychoactive alkaloid. Their removal increases the concentration of the desired psychoactive alkaloids remaining in the extract.

The term "total psychoactive alkaloid content" used herein refers to total amount of psychoactive alkaloid present in the oral transmucosal psychoactive alkaloid composition. The amount is usually a percentage by weight that may be accurate up to two or three significant figures.

The expression "total psychoactive alkaloid content in the psychoactive alkaloid extract" or "total psychoactive alkaloid content by weight of the psychoactive alkaloid extract" used herein refers to amount of a total psychoactive alkaloid content present in a psychoactive alkaloid extract. The amount is usually a percentage by weight that may be accurate up to two significant figures.

The term "active pharmaceutical ingredient" or "API" used herein refers to an active ingredient in a pharmaceutical composition or pharmaceutical drug that is biologically active.

The term "non-active pharmaceutical ingredients" used herein refers to non-medical ingredients of a composition which do not have any have any effect on the body. They are generally used to improve stability of a composition's formulation, bulk up formulations, and more. The term as used herein includes a polymer, a carrier, and one or more excipients.

The term "bioavailability" used herein refers to the fraction of an API that is available in the systemic circulation after administration. This fraction of API in the systemic circulation is therefore available for delivery to the intended site of action.

The term "transmucosal" used herein refers to the route of administration in which an active pharmaceutical ingredient is diffused through a mucosal tissue.

The term "mucosa" or "mucosal tissue" means surface epithelial tissue that is accessible from the outside of the body without surgical procedures.

The term "oral transmucosal psychoactive alkaloid composition" or "composition" or "psychoactive alkaloid composition" used herein means a composition which is suitable for administration of a psychoactive alkaloid via the oral transmucosal route or other mucosal tissue. The oral transmucosal administration route involves a patient holding the composition in the oral cavity while the psychoactive alkaloid dissolves in the available fluids, diffuses through the mucosa lining of the mouth, and enters the bloodstream, bypassing the gastrointestinal tract as well as hepatic metabolism. The release of the API from the formulation is immediate.

The term "sublingual administration" refers to a route of drug administration involving placing a dosage form under the tongue to dissolve and absorb into the systemic circulation through the sublingual tissue.

The expression "buccal administration" here refers to a route of administration involving placing a dosage form in the buccal cavity between gums and cheek, where it also dissolves and is absorbed into the systemic circulation.

The term "mucoadhesive polymers" refers to water-soluble and water insoluble polymers which hold an API in place and thereby facilitate rapid absorption of the API through the permeable oral mucosal tissue. Mucoadhesive polymers may be surfactants or gelling agents.

"Rapid delivery" means initial immediate rapid release and delivery of an API from a composition. The rapid delivery is typically followed by a time-dependent reduction in release of the API from the composition or device and delivery of the drug to the plasma.

The term "excipient" means any component added to an active ingredient to make a composition. An excipient is inert in relation to the active ingredient, in that it essentially does not act in the same way as the active ingredient. An excipient may be completely inert, or it may have some other property that protects the integrity of the active ingredient or assists its uptake into the human body. There are multiple types of excipient, each having a different purpose, and a given excipient may fulfill more than one purpose. Examples of types of excipient include mucoadhesive polymers, surfactants, gelling polymers, flowability agents, flavoring agents, sweeteners, colorants, palatants, antioxidants, bioavailability enhancers, viscosity modifying agents, tonicity agents, drug carriers, sustained-release agents, comfort-enhancing agents, emulsifiers, solubilizing aids, lubricants, carriers, binders, disintegrants and stabilizing agents. Specific excipients include pectin, rice husks, rice, xanthum gum, gum arabic, beta cyclodextrin, alpha cyclodextrin, microcrystalline cellulose, sorbitol, dextrose, guar gum, acacia gum, cellulose gum, talc, magnesium stearate.

The phrase "one or more excipients" is used herein to refer that one excipient or more than one excipient can be used in any combination. The number of excipients to be used will be at the discretion of a person skilled in the art, and they may be of different types.

The term "desired psychoactive effects" herein refers to intended changes in nervous system function resulting in alterations in perception, mood, consciousness, cognition, or behavior that are achieved upon administration of a psychoactive alkaloid composition.

The term "therapeutic effects" is intended to qualify the amount of active ingredients required in the treatment of a disease or disorder or on the effecting of a clinical endpoint.

Reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

B. Composition

In some embodiments, the present invention relates to an oral transmucosal psychoactive alkaloid composition having a psychoactive alkaloid extract, a mucoadhesive polymer, a carrier, and optionally one or more further excipients. In some embodiments, the psychoactive alkaloid extract has a desired amount of a phosphorylated psychoactive alkaloid and a desired amount of a dephosphorylated psychoactive alkaloid. That is, the proportion of dephosphorylated to phosphorylated alkaloids is controlled, and a majority or all of the alkaloids are dephosphorylated. In some embodiments, the psychoactive alkaloid extract additionally includes other psychoactive alkaloids that are not phosphorylatable. In some embodiments, a synthetic psychoactive alkaloid is used instead of the psychoactive alkaloid extract. In some embodiments, the synthetic psychoactive alkaloid has no phosphorylated alkaloid content, or is entirely dephosphorylated psychoactive alkaloid.

B1. Extract

In one embodiment, the psychoactive alkaloid extract forms 1% to 40% by weight of the composition. In another embodiment, the psychoactive alkaloid extract forms 10% to 20% by weight of the composition.

In some embodiments, the psychoactive alkaloid extract has a total psychoactive alkaloid content ranging from 0.1% to 99% by weight of the extract. In other embodiments, the psychoactive alkaloid extract has a total psychoactive alkaloid content ranging from 1% to 75% by weight of the extract. In yet other embodiments, the psychoactive alkaloid extract has a total psychoactive alkaloid content ranging from 1.03% to 3.02% by weight of the extract. In other embodiments, the psychoactive alkaloid composition has a total psychoactive alkaloid content ranging from 10.00% to 20.00% by weight of the composition. The total psychoactive alkaloid content in the psychoactive alkaloid extract may be defined as a percentage up to two decimal places.

In some embodiments, the psychoactive alkaloid extract further includes naturally occurring substances. The naturally occurring substances are present in the psychoactive alkaloid extract in a concentration ranging from 1% to 99.9% by dry weight. These naturally occurring substances do not lead to any side effects or adverse effects when ingested as a part of the composition.

In some embodiments, the desired amount of the dephosphorylated psychoactive alkaloid is over 50% by weight of the total psychoactive alkaloid content in the psychoactive alkaloid extract, and the desired amount of the phosphorylated psychoactive alkaloid is the remainder. In some embodiments, the desired amount of the dephosphorylated psychoactive alkaloid is 100% by weight of the total psychoactive alkaloid content in the psychoactive alkaloid extract. In some embodiments, the desired amount of the dephosphorylated psychoactive alkaloid is 100% by weight of the total phosphorylatable psychoactive alkaloid content in the psychoactive alkaloid extract.

In some embodiments, the psychoactive alkaloid extract is present in its purified form i.e. as a purified psychoactive alkaloid extract. In some embodiments, the purified psychoactive alkaloid extract has a total psychoactive alkaloid content ranging from 10% to 99% by weight of the purified psychoactive alkaloid extract. The naturally occurring substances are present in the purified psychoactive alkaloid extract in a concentration ranging from 1% to 90% by dry weight. In some embodiments, the purified psychoactive alkaloid extract has a total psychoactive alkaloid content ranging from 10.00% to 20.00% by weight of the purified psychoactive alkaloid extract.

In some embodiments, the desired amount of the dephosphorylated psychoactive alkaloid is over 50% by weight of the total psychoactive alkaloid content in the purified psychoactive alkaloid extract, and the desired amount of the phosphorylated psychoactive alkaloid is the remainder. In some embodiments, the desired amount of the dephosphorylated psychoactive alkaloid is 100% by weight of the total psychoactive alkaloid content in the purified psychoactive alkaloid extract. In some embodiments, the desired amount of the dephosphorylated psychoactive alkaloid is 100% by weight of the total phosphorylatable psychoactive alkaloid content in the purified psychoactive alkaloid extract.

The naturally occurring substances referred to herein include fats, sugars, carbohydrates, chitin, chitosan, minerals, waxes, proteins, or any combination selected therefrom. The concentration range of the naturally occurring substances in the psychoactive alkaloid extract or the purified psychoactive alkaloid extract will vary due to various factors for example, but not limited to, the source of the psychoactive alkaloid extract, the extraction technique used, the efficiency of the extraction process, and the amount of the psychoactive alkaloid in the extract.

The composition of the present invention has a total psychoactive alkaloid content present in a specific amount. In some embodiments, the specific amount of the total psychoactive alkaloid content is accurate to one significant figure. In another embodiment, the specific amount of the total psychoactive alkaloid content is accurate to two, three or four significant figures. The presence of the total psychoactive alkaloid content in a specific amount in the composition is possible despite variation of psychoactive content in different batches of the extract.

In some embodiments, the phosphorylated alkaloid is psilocybin, baeocystin, norbaeocystin, aeruginascin, or any combination therefrom; and the dephosphorylated alkaloid is psilocin, bufotenine, bufotenidine, norpsilocin, 4-hydroxytryptamine, N,N,N-trimethyl-4-hydroxytryptamine, or any combination therefrom.

In some embodiments, the 1-40% of extract is replaced with 1-40% of synthetic dephosphorylated psychoactive alkaloid.

B2. Mucoadhesive Polymer

In some embodiments, the mucoadhesive polymer forms 1-50% by weight of the composition. In other embodiments, the mucoadhesive polymer forms 15-35% by weight of the composition. In other embodiments, there are two different mucoadhesive polymers: a first mucoadhesive polymer forming 1-30% by weight of the composition, and a second mucoadhesive polymer forming up to 20% by weight of the composition. In some embodiments, the first mucoadhesive polymer forms 10-20% by weight of the composition and the second mucoadhesive polymer forms 5-15% of the composition. The first and second mucoadhesive polymers are interchangeable and can be selected from the same list, below. The benefit of having two different mucoadhesive polymers is that the mucoadhesive properties are modulated. By combining two mucoadhesive polymers, they form a more heterogenous matrix in which the active ingredient is entrained.

Due to the mucoadhesive binding properties of the psychoactive alkaloid composition to the mucosa upon exposure to the saliva, delivery of the psychoactive alkaloid through the mucosa is facilitated by the mucoadhesive polymer. Thus, along with holding the psychoactive alkaloid in place to facilitate its non-ingestive absorption, the mucoadhesive polymer also ensures minimal swallowing of the psychoactive alkaloids from the oral cavity.

Examples of the mucoadhesive polymer include, but are not limited to, agarose, chitosan, gelatin, hyaluronic acid, guar gum, hakea gum, xanthan gum, gellan gum, carragenan gum, pectin gum, and sodium alginate, CMC (carboxymethylcellulose), thiolated CMC, sodium CMC, HEC (hydroxyethylcellulose), HPC (hydroxypropylcellulose), HPMC (hydroxypropylmethylcellulose), MC (methylcellulose), MHEC (methyl hydroxyethylcellulose), poly(acrylic acid)-based polymers, carbomers, PAA (poly(acrylic acid)), polyacrylates, poly(methylvinylether-co-methacrylic acid), poly(2-hydroxyethyl methacrylate), poly(acrylic acid-co-ethylhexylacrylate), poly(methacrylate), poly(alkylcyanoacrylate), poly(isohexylcyanoacrylate), poly(isobutylcyanoacrylate), copolymer of acrylic acid, PEG (poly(ethylene glycol)), poloxamers, poly(N-2-hydroxypropyl methacrylamide) (PHPMAm), polyoxyethylene, PVA (polyvinyl alcohol), PVP (polyvinylpyrrolidone), thiolated polymers, sodium tauroglycocholate, or any combination therefrom. Appropriate selection of the mucoadhesive polymer to be included in the composition can be made by a person of skill in the art.

B3. Carrier

In other embodiments, the carrier forms 10-65% by weight of the composition. In some embodiments, the carrier forms 10-50% by weight of the composition. In other embodiments, the carrier forms 25-40% by weight of the composition. Carriers facilitate the psychoactive alkaloid compositions to achieve dry and stable forms. Psilocin is highly unstable in nature, however, the addition of carriers to a psilocin composition allows the composition to exist more stably, in a free-flowing powder form. To achieve this, the carrier is present in a significant amount.

In some embodiments, there are two different carriers.

Further, the carrier needs to be compatible with the surfactant system provided by the mucoadhesive polymer and the liquid or powdered formulation. Accordingly, a person of skill in the art can select the carrier to be added to the present composition. Some examples of the carrier include, but are not limited to, pectin, starch, tapioca maltodextrin, rice maltodextrin, rice husks, rice, xanthum gum, gum arabic, beta cyclodextrin, alpha cyclodextrin, microcrystalline cellulose, sorbitol, dextrose, silica, guar gum, acacia gum, cellulose gum, talc, magnesium stearate, stearic acid, citric acid, sorbitol and any combination of the foregoing.

B4. Binder

In one embodiment, the optional one or more further excipients in the composition include a binder. The binder acts an adhesive to bind particles in the composition together and result in a formulation with a necessary mechanical strength. In an exemplary embodiment, the binder allows for the composition to be compressed into a tablet without disintegrating. In some embodiments, the binder is present in the composition in a concentration ranging from 5-20% by weight of the composition. In other embodiments, the binder is present in the composition in a concentration ranging from 5-10% by weight of the composition. The amount of binder is usually lower than the other excipients as only a sufficient amount to hold the composition together is required.

The binder for addition to the present composition needs to be hydrophilic in nature. Further, the binder needs to be compatible with the surfactant system provided by the mucoadhesive polymer, the carrier, and the liquid or powdered formulation. Accordingly, a person of skill in the art can select the binder to be added to the present composition. Some examples of the binder include, but are not limited to, pectin, starch, tapioca maltodextrin, rice maltodextrin, rice husks, rice, xanthum gum, gum arabic, beta cyclodextrin, alpha cyclodextrin, microcrystalline cellulose, sorbitol, dextrose, silica, guar gum, acacia gum, cellulose gum, talc, magnesium stearate, stearic acid, citric acid, sorbitol and any combination of the foregoing.

B5. Preservative/Antioxidant

In some embodiments, the one or more further excipients include a preservative or antioxidant. In some embodiments, the preservative or antioxidant is present in the composition in a concentration ranging from 1-5% by weight of the composition. In other embodiments, the preservative or antioxidant is present in the composition in a concentration ranging from 3-5% by weight of the composition. The preservative or antioxidant provides chemical stability to the composition so that it has a longer shelf life compared to compositions without the preservative or antioxidant.

B6. Other Excipients

In some embodiments, the one or more further excipients include a bioavailability enhancer. Bioavailability enhancers bind to active pharmaceutical ingredients and either increase their stability, ability to cross membranes, or prevent the body from breaking down the API. In one embodiment, the bioavailability enhancer is present in the composition in a concentration ranging from 0-5% by weight of the composition. In another embodiment, the bioavailability enhancer is present in the composition in a concentration ranging from 0.5-2% by weight of the composition. Utilization of bioavailability enhancers in these relatively small concentrations decreases the occurrence of an adverse effect, and only small concentrations are needed to be effective. Examples of bioavailability enhancer include, but are not limited to, beta cyclodextrin, alpha cyclodextrin, piperine, citric acid, and beta-carbolines (MAOI) such as harmaline.

In some embodiments, the one or more excipients include a flavoring agent, artificial or natural sweeteners, or a combination thereof. In one embodiment, the flavoring agents or sweeteners are present in the composition in a concentration ranging from 0-0.5% by weight of the composition. In one embodiment, the flavoring agents or sweeteners are present in the composition in a concentration of 0.1% by weight of the composition. Generally very low percentages of flavoring agent are used so as not to create the unpleasantness of too strong a flavour.

In some embodiments, one or more disintegrants may be optionally included in the excipients. Examples of disintegrants are: starch, sodium croscarmellose or sodium starch glycolate.

B7. Delivery

In some embodiments, the oral transmucosal compositions allow the delivery of psychoactive alkaloids into the patient's bloodstream while bypassing the gastrointestinal tract and the hepatic metabolism. As such, they result in a higher bioavailability of the dephosphorylated psychoactive alkaloids to the patient compared to ingested forms. This also allows for lower dosage requirements of psychoactive alkaloids to achieve the desired psychoactive effects.

In some embodiments, the oral transmucosal composition is formulated into a tablet. Due to enhanced bioavailability of the psychoactive alkaloids from the composition, desired therapeutic effects can be achieved with a tablet weighing equal to or less than 0.5 grams, which, due to its small size, minimizes saliva response in the oral cavity.

In some embodiments, oral transmucosal compositions are administered in the oral cavity at sublingual, palatal, buccal or gingival locations or the like. In one embodiment, the route of administration of the oral transmucosal composition is sublingual administration. In one embodiment, the route of administration of the oral transmucosal composition is buccal administration.

In some embodiments, the oral transmucosal psychoactive alkaloid composition is formulated as a gel, cream, lotion, ointment, foam, film, hydrogel, capsule, tablet, microparticles, microcapsules, nanoparticles, nanocapsules, or the like. Any form of drug dosage form that will effectively deliver the psychoactive alkaloids transmucosally in the oral cavity across into the general blood circulation is intended to be included within the scope of this invention.

In some embodiments, oral transmucosal psychoactive alkaloid compositions include pharmaceutical solvents to produce sprays, solutions, emulsions, suspensions, gels, gel-forming liquids, ointments and pastes, among others.

The composition of the present invention can also be in a powder form or in granular form. The composition of the present invention may be in the form of a free-flowing powder depending on the embodiment. Such compositions are thus easy to handle during manufacturing and packaging processes. Further, the dry, free-flowing powder form allows the composition to be free from clumps and not be as susceptible to microbial growth as a composition that clumps due to moisture absorption.

The psychoactive alkaloid composition of the present invention can be used, for example, in medical research on the use of psychedelic substances in treatments for mental illnesses.

While the description largely relates to oral non-ingestive delivery, it is feasible that the compositions disclosed herein are useful for rectal or vaginal delivery.

C. Extraction

In one embodiment, referring to FIG. 1, a process for obtaining a psychoactive alkaloid extract with dephosphorylation control, according to an embodiment of the present invention is shown.

The process includes step 10 of obtaining powdered biomass from a psychoactive alkaloid source. The powdered biomass is obtained by drying and pulverizing a psychoactive alkaloid source. The drying is carried out via vacuum desiccation, freeze drying, timed forced air drying, or other suitable drying method known to a person of skill in the art, to obtain a dried biomass. The pulverization is carried out by milling, grinding, or other method to reduce the particle size of the dried biomass.

In one embodiment, the drying is carried out in a forced air oven completely shielded from all light at 20-30° C. for a time period of 5-10 hours. However, there is room for optimization of the drying step, using different temperatures (e.g. 10-50° C.) and different durations.

In one embodiment, the psychoactive alkaloid source is a mushroom from the genus *Conocybe, Copelandia, Galerina, Gymnopilus, Inocybe, Panaeolus, Pholiotina, Pluteus* or *Psilocybe*, or any combination of mushrooms selected therefrom. In one embodiment, gills, caps, stems, or the whole of the fungi is used as the alkaloid source.

Step 12 involves extracting the psychoactive alkaloid from the dried powdered biomass with an acidified solvent or a basified solvent to obtain a psychoactive alkaloid liquid with a specific pH, wherein the specific pH is lower than 3.5 or over 10.5. After adding the acidified solvent or the basified solvent, the psychoactive alkaloid liquid has a pH ranging from 0.5-3.5. In another exemplary embodiment, the pH of the psychoactive alkaloid liquid obtained after addition of the acidified solvent is 2.

The pH is adjusted to lower than 3.5 in the extraction step 12 to promote the conversion of phosphorylated psychoactive alkaloid to dephosphorylated psychoactive alkaloid, thus allowing the preparation of the psychoactive alkaloid liquid with the predominantly or entirely dephosphorylated psychoactive alkaloid. For example, with pH conditions lower than 3.5, psilocybin is readily converted to psilocin. In some embodiments, during the extraction step the psychoactive alkaloid liquid has a pH lower than 3.5 and the desired amount of the phosphorylated psychoactive alkaloid is 0% by weight of the total psychoactive alkaloid content in the psychoactive alkaloid extract. The desired amount of the dephosphorylated psychoactive alkaloid is 100% by weight of the total psychoactive alkaloid content in the psychoactive alkaloid extract. Even with neutral hydroethanol extraction, a large portion of psilocybin may be converted to psilocin. However, the low pH environment (<3.5) protects the psilocin from oxidation.

If the pH in step 12 were 10.5 or higher, then the conversion of phosphorylated alkaloids to dephosphorylated alkaloids would be inhibited, and the result would be predominantly or entirely phosphorylated alkaloids.

In some embodiments, the extraction is performed at a temperature ranging from 5-95° C. In other embodiments, the extraction is performed at a temperature ranging from 50-75° C.

In some embodiments, the extraction is performed for a time period ranging from 10-720 minutes. For most cases, a time below 10 min would result in a mostly incomplete yield, and above 720 min the extraction may be incomplete but would be continuing at a negligible rate. In another embodiment, and more usually, the extraction is performed for a time period ranging from 30-240 minutes.

In some embodiments, the extraction is performed at a pressure ranging from 7 to 20,000 psi. In yet another embodiment, the extraction is performed at a pressure ranging from 10 to 20 psi.

In some embodiments, the extraction is performed with a solvent to solid ratio in the range 1 L:1 kg to 50 L:1 kg, wherein the solid is the dried powdered biomass. In one embodiment, the extraction is performed with a solvent to solid ratio of 20 L:1 kg.

After the addition of the acidified solvent or the basified solvent, the powered biomass and the solvent are mixed, followed by step 14 of filtration to result in the extracted filtrate of step 16 (i.e. psychoactive alkaloid liquid).

In step 18 of the process, the pH of the obtained psychoactive alkaloid liquid is adjusted to a pH ranging from 3.5-4.5. The pH is adjusted by adding a base or an acid. The pH is adjusted to a value in this range as the psychoactive alkaloid liquid exhibits a good anti-microbial stability in this pH range. Also, there is no conversion of dephosphorylated alkaloids to phosphorylated alkaloids at this pH after the alkaloids are removed from the biomass, which points to enzymatic hydrolysis being responsible for conversion in the source of the psychoactive alkaloids. In exemplary embodiments, the base is sodium hydroxide and the acid is citric acid. Any other appropriate acid or base can be used to adjust the pH, which a person of skill in the art may determine. The selection of the acid or the base will depend upon the nature of the pH of the psychoactive alkaloid liquid prior to adjusting it to the range of 3.5-4.5, according to which a person of skill in the art can make the appropriate acid or base selection.

In some embodiments, the extraction step comprises further extracting the psychoactive alkaloid by repeating the extraction step. Filtrate residue from step 14 is collected and to this filtrate residue, the same or a different acidified solvent, or the same or a different basified solvent is added. The resulting mixture is mixed followed by filtration to obtain another filtrate. This filtrate and the previous filtrate are mixed together to result in a bulk filtrate. To this bulk filtrate the acid or the base is added to adjust the pH to 3.5-4.5 according to step 18. In some embodiments, the further extraction of the filtrate obtained after extraction with the acidified or the basified solvent is repeated until a required amount of the phosphorylated psychoactive alkaloid and/or the dephosphorylated psychoactive alkaloid is extracted. The number of extraction cycles to be repeated will depend on various variable factors such as the source of the psychoactive alkaloid and the solubility of the psychoactive alkaloid in the acidified or the basified solvent.

Step 20 of the process involves evaporating the solvent from the psychoactive alkaloid liquid to obtain the psychoactive alkaloid extract with the desired amount of the phosphorylated psychoactive alkaloid and the desired amount of the dephosphorylated psychoactive alkaloid. The solvent is completely or partially evaporated to result in the psychoactive alkaloid extract as a slurry or powder. The evaporation is carried out by methods such as air-drying, rotary evaporation, or other methods known in the art to suitably evaporate solvent from psychoactive alkaloid liquid. At this point in time, away from the biomass, dephosphorylated/phosphorylated alkaloids are fairly heat resistant, more so under vacuum, and so rotary evaporation, for example, is a suitable process. For the purposes of the composition disclosed herein, the desired amount of the dephosphorylated psychoactive alkaloid is 100% of the total psychoactive alkaloid content in the psychoactive alkaloid extract, and the desired amount of the phosphorylated psychoactive alkaloid is 0%. As such, an acidified solvent is selected in step 12.

Evaporation may be paused, for standardization, and continued after. The evaporation of a portion of the solvent, before collection of the psychoactive alkaloid extract, in slurry form, for standardization, is done to obtain a quantity of a psychoactive alkaloid extract that is easy to handle in the subsequent steps of the standardization process. The quantity of the portion of the solvent to be evaporated before pausing the evaporation is not so much as to make it too viscous to handle well. The quantity of the portion of the solvent to be evaporated will depend on various factors, for example, but not limited to, the contents of the psychoactive alkaloid liquid and the quantity of the psychoactive alkaloid liquid present at the beginning of the evaporation step.

When used, the acid may be acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination of one or more of these. In some embodiments, the acid is either only hydrochloric acid or only phosphoric acid, for example. It is also envisaged that other acids may be used, for example non-food-grade acids that may be used by pharmaceuticals.

When used, the base may be ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic or any combination therefrom. In one embodiment, the base is solely sodium hydroxide, for example. Other bases may be used in other embodiments, for example non-food-grade bases that may be used by pharmaceuticals.

In some embodiments, the acidified solvent is a mixture of an acid and a C1-C4 primary aliphatic alcohol, a C3-C4 ketone, water, or any combination selected therefrom. The acid may be citric acid, ascorbic acid, formic acid, acetic acid, hydrochloric acid, phosphoric acid, sulphuric acid, or any combination selected therefrom. In other embodiments, the basified solvent is a mixture of a base and a C1-C4 primary aliphatic alcohol, a C3-C4 ketone, water, or any combination selected therefrom. The base may be sodium hydroxide, potassium hydroxide, ammonium hydroxide, sodium bicarbonate, calcium carbonate, or any combination selected therefrom.

D. Purification

D1. Main Process

Figure 2:
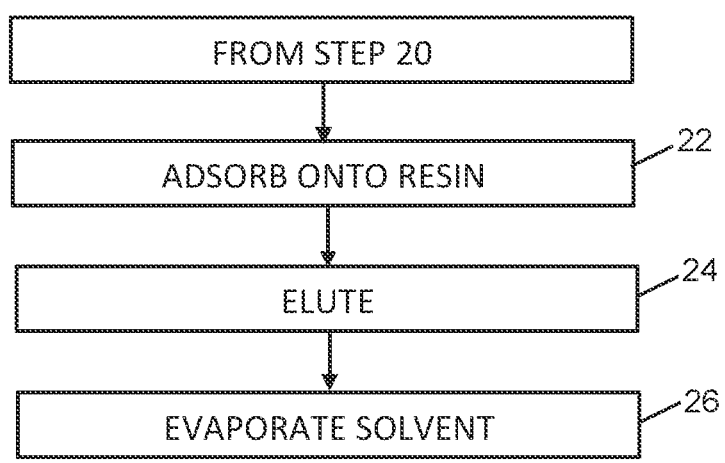
FIG. 2 illustrates the steps of a basic process for obtaining a purified psychoactive alkaloid extract according to an embodiment of the present invention.

In one embodiment, referring to FIG. 2, steps of a basic process for obtaining a purified psychoactive alkaloid extract are shown. The psychoactive alkaloid extract obtained in step 18 or 20 is adsorbed, in step 22, onto a resin to obtain an adsorbed psychoactive alkaloid, which may include one or more adsorbed psychoactive alkaloids.

In one embodiment, the resin is an adsorbent resin of the macroporous type, such as, a cation or anion ion-exchange resin, a non-ionic resin, or any combination therefrom. Representative pharmaceutical, nutraceutical or food-grade grade resins for use in accordance with the present invention are known to those skilled in the art. For example, pharmaceutical grade non-ionic macroporous resins are commercially available, e.g. Amberlite® XAD4. In one embodiment, the resin is a cationic ion-exchange resin or an anionic-exchange resin. The cationic ion-exchange resin may be selected from commercially available cationic ion-exchange resins known in the art, including but not limited to Amberlite® MAC-3 H. The cationic ion-exchange resin may be in an $H^+$ form or an $Na^+$ form. The anionic ion-exchange resin may be selected from commercially available anion exchange resins known in the art, including but not limited to Amberchrom® 50WX8. The anionic ion-exchange resin may be in an $OH^-$ form or a $Cl^-$ form. The resins used may be of any particle size. In some embodiments, the resins may be gel type resins, with any size of gel bead.

Next, the process involves eluting, in step 24, the adsorbed psychoactive alkaloid using a solvent to obtain a purified psychoactive alkaloid solution. The solvent may be, for example, an organic solvent, an acid, a base, a combination of an organic solvent and a base, a combination an organic solvent and an acid, water, a combination of water and acid, a combination of water and base, or a combination of water and an organic solvent. Usually, the solvent is different from the solvent in which the extract is initially provided, and is either a different type of solvent or a different composition of solvent. It may be at a different temperature than the initial solvent.

In some embodiments, the solvent used in the elution step 24 may be a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the primary aliphatic alcohol is ethanol. In one embodiment, the ketone is a C3-4 ketone. In yet another embodiment, the water is deionized, distilled, reverse osmosis, or otherwise purified water, which is substantially without free ions. In other embodiments, the water is not purified.

In one embodiment, the solvent used in the elution step 24 is a combination of an organic solvent and an acid. In one embodiment, the combination of an acid and an organic solvent is 2% hydrochloric acid and 80% ethanol, for example. In general, any acidic environment will displace some of the ions from the resin, but the rate and optimization of desorption will be affected by the acid concentration. In one embodiment, the solvent used in the elution step 24 is a combination of an organic solvent and a base. In one embodiment, the combination of an organic solvent and a base is of 2% sodium chloride and 80% ethanol, for example. In general, any basic environment will displace some of the ions from the resin, but the rate and optimization of desorption will be affected by the concentration of the base.

All the above solvents and combinations thereof are suitable for the elution step because all of the psychoactive alkaloids of interest are soluble therein and, depending on the choice of resin, they are all capable of pulling the alkaloids of interest off a resin. There are many different resins available, and it is a straightforward matter to select a suitable resin and elution solvent pair.

In one embodiment, the elution step is carried out at a temperature in the range of 4-75° C. These temperatures are limited by the boiling point of the solvent used, as well as the specifications of allowable food-grade resins, as determined by the manufacturers of the resins and governmental food and drug administrations. In another embodiment, the elution step is carried out at room temperature for convenience, i.e. at 21-25° C.

In other embodiments, the process for obtaining the purified psychoactive alkaloid solution further includes repeating the steps 22 and 24 with the obtained purified psychoactive alkaloid solution to obtain a further or twice purified psychoactive alkaloid solution. For the repeated steps in these embodiments, the resin may be the same or a different resin, and the solvent may be the same or a different solvent. While the purified psychoactive alkaloid solution may have a low psychoactive alkaloid content, this may be increased by evaporation of some or all of the solvent.

Step 26 involves evaporating the solvent from the purified psychoactive alkaloid solution to obtain the purified psychoactive alkaloid extract with the desired amount of the phosphorylated psychoactive alkaloid and the desired amount of the dephosphorylated psychoactive alkaloid (for example, 0% and 100% respectively for the composition herein). The solvent is completely or partially evaporated to result in the psychoactive alkaloid extract (slurry or powder). The evaporation is carried out by methods such as air-drying, rotary evaporation, or other methods known in the art to suitably evaporate solvent from psychoactive alkaloid liquid.

Optionally, the obtained purified psychoactive alkaloid solution is further purified by filtering the obtained purified psychoactive alkaloid solution to obtain a filtrate, and then repeating at least steps 22 and 24 with the obtained filtrate. Steps 22 and 24 can be repeated with the same or a different resinous material and solvent.

Evaporation in step 26 may be paused, for standardization, and continued after. The evaporation of a portion of the solvent, before collection of the purified psychoactive alkaloid slurry for standardization, is done to obtain a quantity of a psychoactive alkaloid slurry that is easy to handle in the subsequent steps of the standardization process. The quantity of the portion of the solvent to be evaporated before pausing the evaporation is not so much as to make it too viscous to handle well. The quantity of the portion of the solvent to be evaporated will depend on various factors, for example, but not limited to, the contents of the psychoactive alkaloid solution and the quantity of the psychoactive alkaloid solution present at the beginning of the evaporation step.

D2. Further Process

Figure 3:
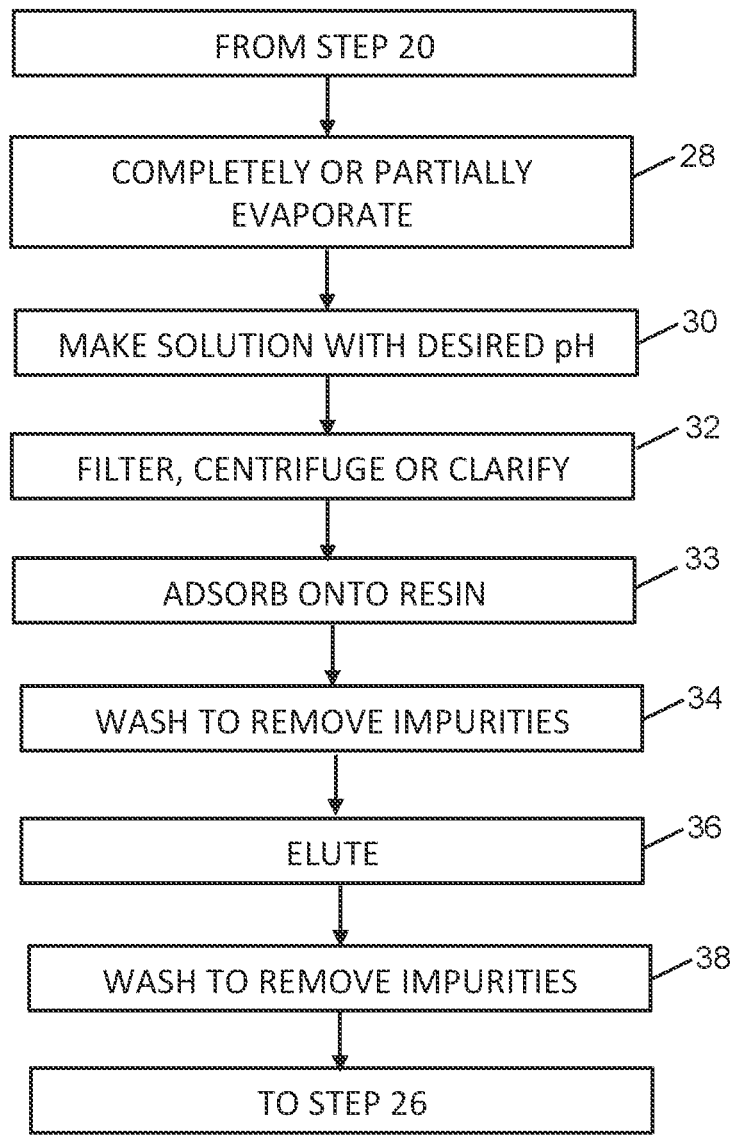
FIG. 3 illustrates the basic and optional steps of a process for purification of a psychoactive alkaloid extract, according to an embodiment of the present invention.

In an embodiment, referring to FIG. 3, the basic and optional steps of a process for purification of a psychoactive alkaloid extract are depicted. In one embodiment, the psychoactive alkaloid extract obtained in step 18 or 20 is followed by completely or partially concentrating the obtained psychoactive alkaloid extract by evaporation of the solvent from the extract in step 28. If the solvent from the extract has been completely evaporated in step 28, then reverse osmosis water, more solvent or another solvent is added back. Other water may be used in place of reverse osmosis water, which was selected for its purity.

In some embodiments, the process includes adding, in step 30, an acid or a base to the psychoactive alkaloid extract obtained in step 20 to obtain a psychoactive alkaloid solution with a desired pH.

When used, the acid may be acetic acid, adipic acid, ascorbic acid, phosphoric acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulphuric acid monobasic, calcium phosphate tribasic, citric acid, fumaric acid, gluconic acid, magnesium fumarate, malic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate, tartaric acid, and any combination of one or more of these. In some embodiments, the acid is either only hydrochloric acid or only phosphoric acid, for example. It is also envisaged that other acids may be used.

When used, the base may be ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic or any combination therefrom. In one embodiment, the base is solely sodium hydroxide, for example. Other bases may be used in other embodiments.

In one embodiment, the desired pH psychoactive alkaloid solution has a pH ranging from 2.5-4.5, or from 9-10. In other embodiments, the desired pH psychoactive alkaloid solution has a pH of 3, 4, or 9.5. A person of skill in the art will appreciate that the selection of the pH is chosen in a manner to allow for the efficient adsorption of the psychoactive alkaloids onto the resin(s).

In one embodiment, the process includes adding phosphoric acid to the psychoactive alkaloid extract to achieve a pH of 4. In another embodiment, the process includes adding hydrochloric acid to the psychoactive alkaloid extract to achieve a pH of 3. In yet another embodiment, the process includes adding sodium hydroxide to the psychoactive alkaloid extract to achieve a pH of 9.5.

The process includes, in step 32, optionally filtering, centrifuging, or clarifying the psychoactive alkaloid solution or desired pH psychoactive alkaloid solution, as the case may be, and utilizing the obtained filtrate for the next step 33 of adsorption. Clarifying may be performed, for example, by adding an agglomeration agent. In step 33, the process involves adsorbing the psychoactive alkaloid(s) in the solution onto the resin to obtain an adsorbed psychoactive alkaloid.

In step 34, the process involves washing the resin to remove adsorbed impurities from the resin. While not all the impurities are adsorbed onto the resin, some of them may be. The washing step, substantially, does not remove the adsorbed psychoactive alkaloids. The washing solvent may be 100% ethanol, 100% reverse osmosis water, or any other washing solvent used in ion-exchange resin chromatography, provided that the washing removes impurities or by-products that are adsorbed on the resin. Impurities or by-products may include, for example, sugars, carbohydrates, chitin, chitosan, fats, minerals, waxes, or proteins. There may be one, two or more washing steps depending on the embodiment, and the same or different washing solvents may be used for each wash. In other embodiments, the solvent(s) for washing may include a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the primary aliphatic alcohol is ethanol. In one embodiment, the ketone is a C3-4 ketone. In yet another embodiment, the water is selected from deionized, distilled, reverse osmosis, or otherwise purified water that is substantially without free ions.

After the washing, the process involves eluting, in step 36, the adsorbed psychoactive alkaloid from the resin using a solvent to obtain a purified psychoactive alkaloid solution. The solvent may be an organic solvent, an acid, a base, or water, a combination of an organic solvent and a base, or a combination of an organic solvent and an acid, a combination of an organic solvent and water, a combination of water and a base, or combination of water and an acid. The result of the elution step is a purified psychoactive alkaloid solution.

Following the elution, a further washing step 38 may be employed using 100% ethanol, for example, to wash the resin. This may be considered to be a cleaning step, to refresh the resin and make it ready to be used again in a subsequent step or in another process. In other embodiments, the solvent for further washing may be a primary aliphatic alcohol, a ketone, water, and any combination therefrom. In one embodiment, the primary aliphatic alcohol is a C1-4 alcohol. In one embodiment, the primary aliphatic alcohol is 5% ethanol. In one embodiment, the ketone is a C3-4 ketone. In yet another embodiment, the water is selected from deionized, distilled, reverse osmosis, or otherwise purified water that is substantially without free ions.

The result of the elution is a purified psychoactive alkaloid solution. In one embodiment, the purified psychoactive alkaloid solution has a concentration of 0.07% by weight of a psychoactive alkaloid, which is the concentration before removal of some or all of the solvent. This concentration may be different in other embodiments, depending on the amount solvent used for the elution and the potency of the raw materials. In one embodiment, the purified psychoactive alkaloid solution is concentrated by evaporating the solvent to form a purified psychoactive slurry that has at least of 5% by weight or more of a psychoactive alkaloid. In another embodiment, the purified psychoactive alkaloid slurry has 5-68% by weight of a psychoactive alkaloid. In yet other embodiments, the purified psychoactive alkaloid slurry has a concentration of psychoactive alkaloid outside these ranges, and, when dried, can be as low as 0.1% or as high as 99% dry wt/wt %.

After the removal of impurities in step 38, the obtained purified psychoactive alkaloid solution undergoes the evaporation step 26 to obtain complete or partially evaporate the solvents and result in the purified psychoactive alkaloid extract (slurry or powder form).

E. Preparation of Formulation

Figure 4:
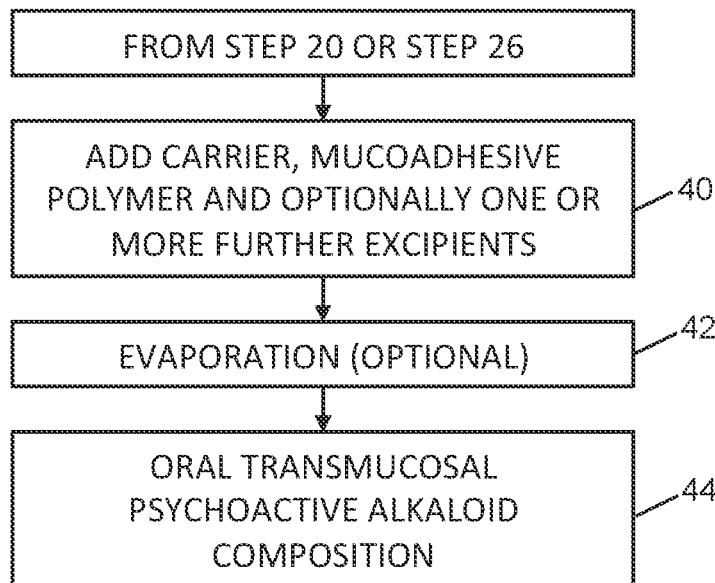
FIG. 4 illustrates the key steps of a process for obtaining an oral transmucosal psychoactive alkaloid composition, according to an embodiment of the present invention.

In one embodiment, referring to FIG. 4 the key steps of a process for obtaining an oral transmucosal psychoactive alkaloid composition are shown.

Step 40 involves adding of a carrier, a mucoadhesive polymer, and optionally one or more other excipients to the psychoactive alkaloid extract (slurry or powder) from step 20 or 26. This is followed by mixing. In one embodiment, a binder, a bioavailability enhancer, or a flavoring agent, a sweetener, or any combination therefrom can also be added in step 40 as an optional excipient. A person of skill in the art will appreciate that the mixing can be performed by any suitable method, which does not cause any damage to the active pharmaceutical ingredients or the active pharmaceutical ingredients, known in the literature.

Step 40 also ensures standardization of the psychoactive alkaloid extract by adding thereto measured quantities of a mucoadhesive polymer, a carrier, and optionally one or more excipients. Standardization is more conveniently done when the extract is a slurry than a powder, but it is not necessary that it is a slurry. Firstly, for example for a slurry, the weight percentage of the psychoactive alkaloids in the psychoactive alkaloid extract and the weight proportion of solids in the psychoactive alkaloid extract are measured. The psychoactive alkaloid content in the final composition is specified. A measured amount of a mucoadhesive polymer, a carrier, and optionally one or more further excipients is added to the psychoactive alkaloid extract, such that, when the remaining solvent is evaporated, the resultant solid will have the specified content of psychoactive alkaloids. The specific amount of the total psychoactive alkaloid content in the composition may be accurate to one or two decimal places, or one or two significant figures depending on how accurately the measurements are made during the mixing of the psychoactive alkaloid extract, the carrier, the mucoadhesive polymer, and the optional one or more excipients.

Thus, the psychoactive alkaloid composition obtained has a specific amount of the total psychoactive alkaloid content. Further, the psychoactive alkaloid is made up of a psychoactive alkaloid with a controlled amount of dephosphorylation, and possibly other psychoactive alkaloids that are not dephosphorylatable.

In some embodiments, when the psychoactive alkaloid extract from step 20 or the purified psychoactive alkaloid extract from 26 is in a form of a slurry, an optional step 42 of evaporation is also followed. Step 42 ensures complete evaporation of solvent resulting in an oral transmucosal psychoactive alkaloid composition 44 which is in the form of granules or free flowing powder.

F. Examples

In order to further illustrate the present invention, the following specific examples are given with the understanding that these examples are intended only to be illustrations without serving as a limitation on the scope of the present invention. All parameters, dimensions, materials, quantities and configurations described herein are examples only and may be changed depending on the specific embodiment. Accordingly, the scope of the invention is to be construed in accordance with the substance defined by the appended claims. The process may be scaled up using larger quantities and modified apparatus.

Although the examples of the present invention have been formulated specifically using *Psilocybe cubensis* as a source to obtain a psychoactive alkaloid extract, the extract comprising predominantly dephosphorylated psychoactive alkaloid (e.g. psilocin), other sources are possible. A person skilled in the art would appreciate that the *Psilocybe cubensis* can be readily substituted by other sources of psychoactive alkaloids to obtain a variety of psychoactive alkaloids having similar properties, such psilocybin, baeocystin, norbaeocystin, aeruginascin, psilocin, norpsilocin, 4-hydroxytryptamine, N, N, N-trimethyl-4-hydroxytryptamine, or any combination therefrom, to name a few, to result in compositions with similar efficacy and efficiency as well. For example, mushrooms from the genus *Conocybe, Cope-*

*landia, Galerina, Gymnopilus, Inocybe, Panaeolus, Pholiotina, Pluteus, Psilocybe*, or any combination therefrom may be used.

Example 1: Process for Promotion of Dephosphorylation 2.5 kilograms of *Psilocybe cubensis* were dried in a forced air oven at 25° C. for 10 hours to result in 140 grams of dried biomass. The dried biomass was then pulverized to a size of 200 mesh with a hammer mill.

An acidified solvent, i.e. a pH-adjusted, hydro-ethanol mixture, was prepared. 144 g of anhydrous citric acid was placed into a 5 L vessel with 1.25 L of reverse osmosis water followed by the addition of 3.75 L of ethanol. The contents were mixed until completely dissolved. An acidified solvent with a pH of 2 was obtained.

The dried powdered biomass was placed into an agitated, heat-controlled vessel with 5 L of the acidified solvent and mixed for the extraction of psychoactive alkaloid. The extraction was controlled to a constant 75° C., and the duration of extraction was 1 hour. The extraction slurry was then filtered. Filtration resulted in a filtrate, i.e. the psychoactive alkaloid liquid, and a filter residue. The filter residue was placed back into the extraction vessel and extracted with an additional 5 L of the acidified solvent. The temperature of extraction was again 75° C. and the time was 1 hour. The extraction slurry was filtered. The filtrates from the first and second extraction were mixed to form 10 L of mixed filtrate. The pH of the mixed filtrate was then increased with 5 M sodium hydroxide until a pH of 4.5 was achieved. Immediately after adjusting the pH, the mixed filtrate was placed into a rotary evaporator at 50° C. and 250 torr, and the solvent was partially or completely evaporated to obtain a psychoactive alkaloid extract. Final stages of evaporation were performed using a freeze dryer and the psychoactive alkaloid extract was obtained. When dried to a powder, the psychoactive alkaloid extract had a total psychoactive alkaloid concentration of 0.86% by weight of the psychoactive alkaloid extract. Further, the desired amount of the phosphorylated psychoactive alkaloid obtained was 0.00% by weight of the total psychoactive alkaloid content in the psychoactive alkaloid extract. The desired amount of the dephosphorylated psychoactive alkaloid obtained was 100% by weight of the total psychoactive alkaloid content in the psychoactive alkaloid extract.

Example 2.1: Purification with a Non-Ionic Macroporous Resin

The pH of the psychoactive alkaloid extract of example 1, in aqueous form, was adjusted to pH 4.0 (+/−0.5) by adding 2 M phosphoric acid and centrifuged for 15 minutes at 3000 g to remove any solid precipitate. The pH of 4 corresponds to the isoelectric point of psilocybin, and psilocin's polarity is such that it is partitioned onto the resin, thus allowing effective binding of the psychoactive alkaloids psilocybin and psilocin to the macroporous resin. Norbaeocystin and baeocystin are phosphorylated and behave in the same way as psilocybin. The supernatant obtained was loaded onto a column of Amberlite® XAD4, a non-ionic macroporous resin (50.34 g of dry resin) at a flow rate of 2 bed volumes per hour, to allow components in the supernatant to be adsorbed onto the macroporous resin. After all 2.5 L of the extract was loaded onto the column of macroporous resin, the column was washed in a single pass with 5 bed volumes of reverse osmosis water at room temperature. This was followed by elution with 5 bed volumes of 5% ethanol (by weight), again at room temperature. Finally, the column was washed in a single pass with 5 bed volumes of 100% ethanol. The elution was performed at room temperature. Each of these three fractions was collected separately. The particular order for the washing steps and the elution was selected to be in the order of the polarity of the solvents. If the order were different, an inferior result may have ensued, such as a lower yield. The first fraction using reverse osmosis water removed the most polar compounds from the resin. The hydroethanol fraction eluted compounds of lesser polarity, and the 100% ethanol solvent removed the least polar compounds. Less polar solvents could also be used to elute less polar compounds.

The 5% ethanol fraction (i.e. the purified psychoactive alkaloid solution) was then concentrated in a rotary evaporator to form 3.90 g of concentrated aqueous slurry at 30% solids, containing 195.1 mg of total alkaloids, i.e. psilocybin, psilocin, norbaeocystin, and baeocystin. The result was a purified psychoactive alkaloid extract, in slurry form. Further, the desired amount of the psychoactive alkaloid obtained was 5.00% by weight of the slurry. Knowing this, it is possible to replace the solvent with an equivalent weight of excipients to provide a purified extract with a psychoactive alkaloid content of 5.00% dry weight.

Example 2.2: Purification with Cation Exchange and Non-Ionic Macroporous Resins

The pH of the psychoactive alkaloid extract of example 1, in aqueous form, was adjusted to a pH of 3.0 (+/−0.5) by adding 1M HCl. It was then mixed with 200 g of Amberlite® MAC-3 H, a strong cationic ion-exchange resin in its hydrogen form, to result in a filtrate-resin mixture, in which components of the psychoactive alkaloid filtrate were adsorbed onto the cation exchange resin. The pH of 3 ensured that the psychoactive alkaloid (i.e. psilocybin) was in its protonated form, and thus adsorbed onto the cationic exchange resin efficiently. The filtrate-resin mixture was agitated for 4 hours at room temperature (21° C.-25° C.) and then filtered. The filtrate was discarded, and the resin was rinsed with 2.0 L of 100% EtOH and then 2.0 L of $H_2O$ to remove any impurities. Finally, the psilocybin/psilocin fraction was eluted with 2.0 L of 2% HCl/80% EtOH, for 4 hours at room temperature.

The eluted fraction was brought to a pH of 4.0 (i.e. the isoelectric point of psilocybin) by adding 2M NaOH. The filtrate was then centrifuged at 3000 g to remove any solid precipitate. The resultant filtrate, in form of an aqueous solution, was then placed into a rotary evaporator and the solvent was removed until the aqueous solution reached a volume of 400 mL. The aqueous solution was then again centrifuged for 15 minutes at 3000 g to remove any solid precipitate. The supernatant was loaded onto a column of Amberlite® XAD4 macroporous resin (45.53 g of dry resin) at a flow rate of 2 bed volumes per hour. After all the 400 mL of the supernatant was loaded onto the column, it was initially washed with 5 bed volumes of reverse osmosis water, followed by elution with 5 bed volumes of 5% ethanol (by weight) and then washed with 100% ethanol. Each of these fractions was collected separately. The 5% ethanol fraction (i.e. the purified psychoactive alkaloid solution) was concentrated in a rotary evaporator to form 258 mg of solution containing 175 mg of total alkaloids (i.e. psilocybin, psilocin, norbaeocystin, and baeocystin). Thus, a purified psychoactive alkaloid extract, in slurry form, with a total alkaloid concentration of 68% dry wt/wt % was obtained.

Example 2.3: Purification with Anion Exchange and Non-Ionic Macroporous Resins The pH of the psychoactive alkaloid extract of example 1, which was in aqueous form, was adjusted to 9.5 (+/−0.5) by adding 1 M NaOH and then mixed with 150 g of Amberchrom® 50WX8 strong anionic ion-exchange resin in its hydrogen form to result in a filtrate-resin mixture, in which components of the psychoactive alkaloid filtrate were adsorbed onto the anion exchange resin. The pH of 9.5 (+/−0.5) ensured that the psilocybin, psilocin, norbaeocystin, and baeocystin were deprotonated and had a net negative charge for efficient adsorption onto the strong anion exchanger.

The filtrate-resin mixture was agitated for 4 hours and then filtered out, and the filtrate was discarded. The resin was rinsed with 2.0 L of 100% EtOH and then 2.0 L of $H_2O$ to remove impurities. Finally, the psilocybin/psilocin fraction was eluted with 2.0 L of 2% NaCl/80% EtOH for 4 hours.

The eluted fraction was brought to a pH of 4.0 with the addition 2 M HCl. The extract was then centrifuged at 3000 g to remove any solid precipitate. The resultant extract, in form of a solution, was then placed into a rotary evaporator and the solvent was removed to result in a volume of 400 mL.

The resultant 400 mL aqueous solution was centrifuged for 15 minutes at 3000 g to remove any solid precipitate. The supernatant was loaded onto a column of Amberlite® XAD4 macroporous resin (45.53 g of dry resin) at a flow rate of 2 bed volumes per hour, to allow components of the supernatant to be adsorbed onto the macroporous resin. After all 400 mL of supernatant was loaded onto the column, the column was initially washed with 5 bed volumes of reverse osmosis water, followed by elution with 5 bed volumes of 5% ethanol (by weight) and then a final wash with 100% ethanol was performed. Each of these fractions was collected separately. The 5% ethanol fraction (i.e. the purified psychoactive alkaloid solution) was concentrated in a rotary evaporator to form 325 mg of solution containing 175 mg of total alkaloids (i.e. psilocybin, psilocin, norbaeocystin, and baeocystin). A purified psychoactive alkaloid extract, in slurry form, with a concentration of 54% dry wt/wt % of total alkaloids was therefore obtained.

Example 3: Processes for Oral Transmucosal Psychoactive Alkaloid Formulation In the following examples the oral transmucosal psychoactive alkaloid composition was obtained from dry compaction and wet granulation compaction methods. However, a person of ordinary skill in the art would appreciate that any suitable method known in the literature for mixing of the psychoactive alkaloids with the non-active pharmaceutical ingredients to obtain the oral transmucosal psychoactive alkaloid composition can also be followed.

Example 3.1: Dry Compaction

Figure 5:
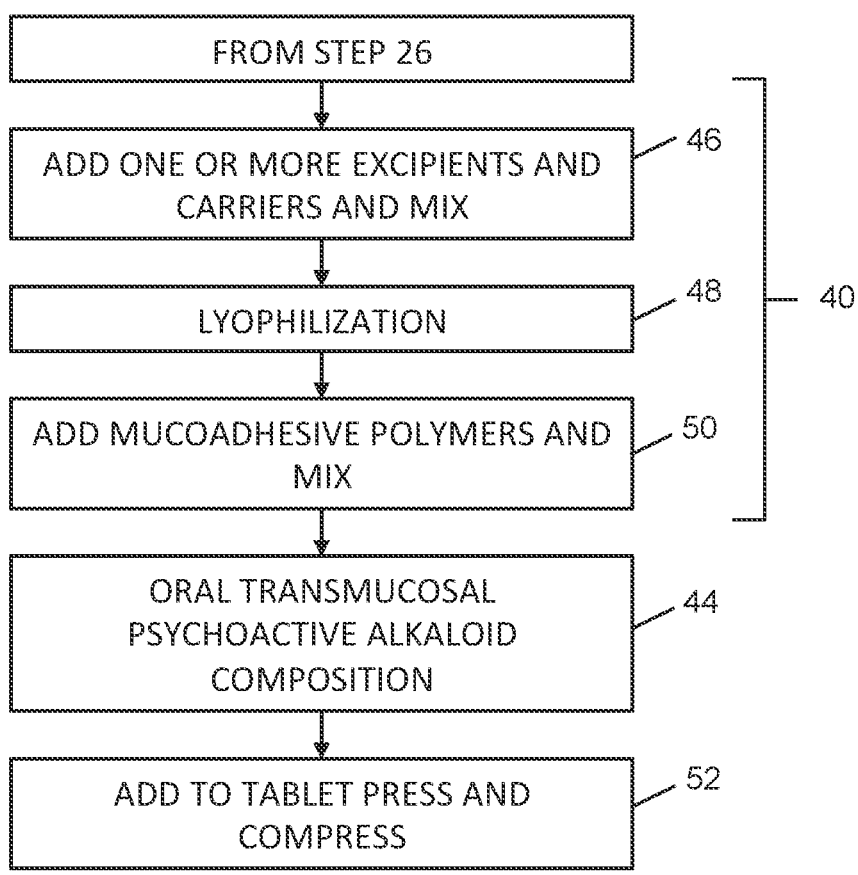
FIG. 5 illustrates detailed steps of a process for obtaining an oral transmucosal psychoactive alkaloid composition via dry compaction, according to an embodiment of the present invention.

In one embodiment, referring to FIG. 5, detailed steps of a process for obtaining an oral transmucosal psychoactive alkaloid composition via dry compaction are illustrated. In step 46, to 0.84 g of purified psychoactive alkaloid extract slurry with 10% solids and 30% (dry wt/wt %) psychoactive alkaloids, 0.138 g of mannitol (sweetener), 0.178 g of maltodextrin (carrier), and 0.025 g of citric acid (preservative) were added together and mixed until a homogenous slurry was achieved. The slurry was obtained by following example 2.1, but stopping the evaporation earlier to achieve 10% solids instead of 30%. This slurry was then lyophilized in step 48 and then ground to a fine powder. In step 50 to this obtained powder, 0.075 g of HPMC-E4 powder (mucoadhesive polymer), was added and thoroughly dry mixed until 0.5 g of a homogenous final mixture (i.e. oral transmucosal psychoactive alkaloid composition) was obtained. The addition of measured amounts of the excipient, the carriers, and the mucoadhesive polymers in steps 46 and 50 respectively resulted in a standardization of the oral transmucosal psychoactive alkaloid composition of step 44. The resultant oral transmucosal psychoactive alkaloid composition has:
- 16.75% by weight of purified psychoactive alkaloid extract;
- 27.50% by weight of mannitol;
- 35.75% by weight of maltodextrin;
- 5% by weight of citric acid; and
- 15.00% by weight of HPMC-E4 powder.

In step 52, the obtained oral transmucosal psychoactive alkaloid composition was then fed to a tablet press and compressed at 1-20 KN. This produced 10 tablets each with 25 mg of psychoactive alkaloids per tablet.

Example 3.2: Wet Granulation Compaction

Figure 6:
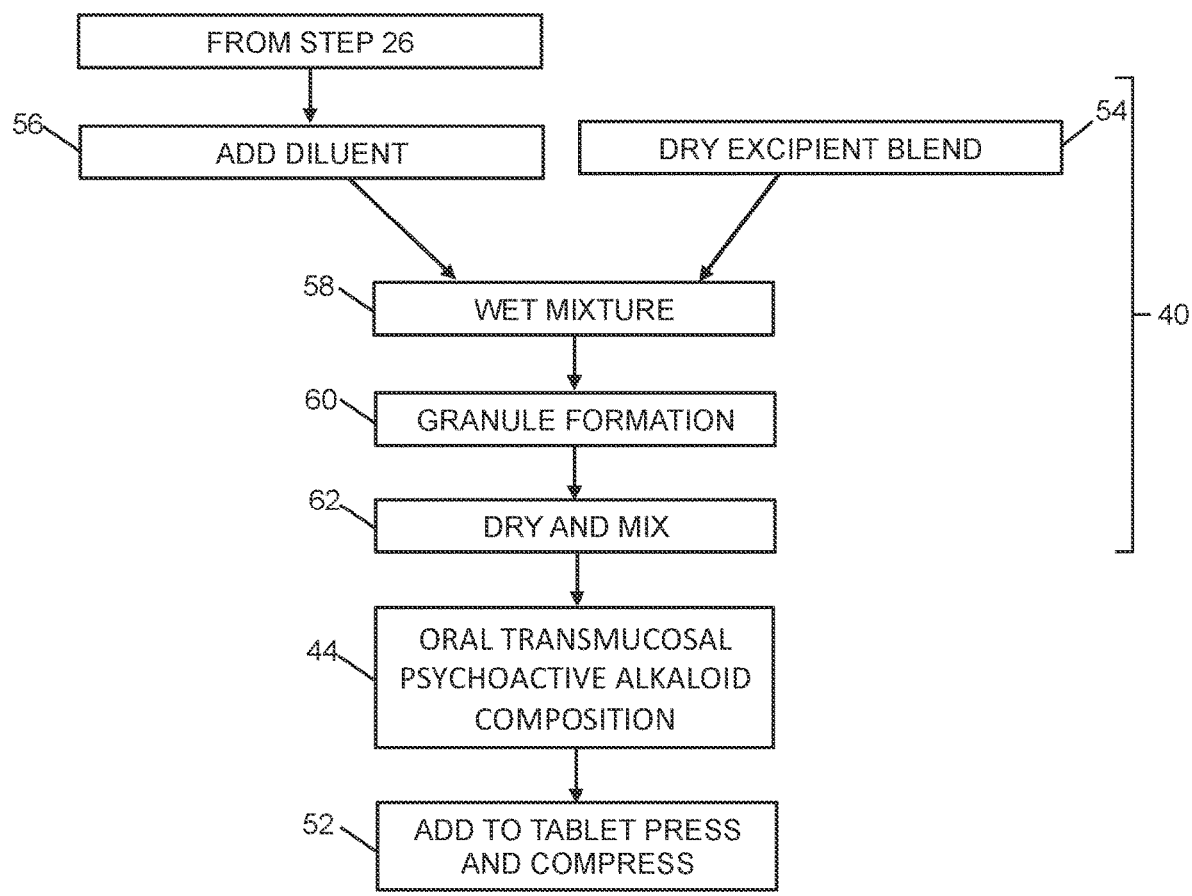
FIG. 6 illustrates detailed steps of a process for obtaining an oral transmucosal psychoactive alkaloid composition via wet granulation compaction, according to an embodiment of the present invention.

In one embodiment, referring to FIG. 6, detailed steps of a process for obtaining an oral transmucosal psychoactive alkaloid composition via wet granulation compaction are illustrated.

In step 54, 0.66 g of Carbopol 984 (mucoadhesive polymer—gelling agent) was combined with 0.75 g of PVP K90 (mucoadhesive polymer—gelling agent), 2.25 g of mannitol (bulking agent, cryoprotectant, sweetener), 0.25 g of stearic acid (further excipient—binder), and 0.25 g of citric acid (preservative) and mixed in a dry mixer until homogenous to result in a dry excipient blend.

In step 56 0.084 g of the purified psychoactive alkaloid extract (30% by weight of the total psychoactive alkaloid content) was dissolved in an appropriate diluent. The purified psychoactive alkaloid extract to diluent ratio was 1:10, with water as the diluent. Other appropriate diluents which can be used include ethanol, isopropyl alcohol, and mixtures of these with water, and other similar hydroalcoholic mixtures, in any ratios. The diluent can be selected by a person of skill in the art according to preference. In step 58 the purified psychoactive alkaloid extract and diluted mixture was then added either via direct pouring or by spraying onto the dry blend of the excipients to obtain a wet mixture. This wet mix was then mixed in a high-shear mixer in step 60 and processed to form granules of the desired size. The formed granules were then dried in a tray oven and mixed in step 62. The oral transmucosal psychoactive alkaloid composition of step 44 was then obtained. The resultant oral transmucosal psychoactive alkaloid composition has:
- 16.75% by weight of purified psychoactive alkaloid extract;
- 13.25% by weight of carbopol;
- 15.00% by weight of PVP K90 (i.e. total of 28.25% mucoadhesive polymer);
- 45.00% by weight of mannitol;
- 5.00% by weight of stearic acid; and
- 5.00% by weight of citric acid.

In step 52, this obtained composition of the oral transmucosal psychoactive alkaloid composition was then fed to a tablet press and compressed at 1-20 KN. This produced 10 tablets each with 25 mg of psychoactive alkaloids per tablet.

The addition of measured amounts of the excipient, the carriers, and the mucoadhesive polymers in step 58 resulted in a standardization of the oral transmucosal psychoactive alkaloid composition of step 44.

Example 3.3

This further example can be seen in TABLE 1, and is prepared using similar steps as for Example 3.2.
16.75% by weight of extract with 30% alkaloid content;
25.00% by weight of PEG 8000 (mucoadhesive polymer);
20.00% by weight of Polyox™ 80 (mucoadhesive polymer);
35.00% by weight of starch;
3.25% by weight of citric acid.

Example 3.4

This further example can be seen in TABLE 1, and is prepared using similar steps as for Example 3.2.
16.75% by weight of extract with 30% alkaloid content;
30.00% by weight of Polyox™ 301;
51.25% by weight of starch
2.00% by weight of citric acid fed into a filter 122 and a first filtrate was collected in container 124. The first filtrate residue 130 was then fed back (R) into the agitated, heat-controlled vessel 110 and more solvent (S) was added for a second extraction. After the second extraction, the extraction slurry was collected in the container 120 and was then fed into a filter 132. After filtration, the obtained second filtrate was collected in container 136.

After the two filtration stages, the filtrates were mixed in container 140 to obtain a mixed filtrate i.e. the psychoactive alkaloid liquid. In other embodiments, if there is only a single filtration step, this mixing step is not required. By adding an acid or a base, the pH of the psychoactive alkaloid liquid was brought to a pH ranging from 3.5-4.5.

The pH-adjusted, mixed filtrate was then placed in a rotary evaporator 142 and part of the solvent was evaporated from the mixed filtrate to form the psychoactive alkaloid extract, which was here a slurry.

For obtaining the psychoactive alkaloid composition, the evaporation in the rotary evaporator 142 was stopped after a desired portion of solvent was evaporated. The resultant slurry was transferred to a container 144 where a measured quantity of a carrier, a mucoadhesive polymer, and optionally one or more excipients were added to obtain a standardized psychoactive alkaloid composition in slurry form. The obtained standardized slurry was dried to obtain the psychoactive alkaloid composition.

TABLE 1

| Composition | | Extract | Mucoadhesive 1 | Mucoadhesive 2 | Carrier 1 | Carrier 2 | Antioxidant/ Preservative | Total |
|---|---|---|---|---|---|---|---|---|
| Example 3.1 | Mass (g) | 0.084 | 0.075 | 0.000 | 0.138 | 0.178 | 0.025 | 0.500 |
|  | wt/wt % (%) | 16.75 | 15.00 | 0.00 | 27.50 | 35.75 | 5.00 | 100 |
| Example 3.2 | Mass (g) | 0.084 | 0.066 | 0.075 | 0.225 | 0.025 | 0.025 | 0.500 |
|  | wt/wt % (%) | 16.75 | 13.25 | 15.00 | 45.00 | 5.00 | 5.00 | 100 |
| Example 3.3 | Mass (g) | 0.084 | 0.125 | 0.100 | 0.050 | 0.125 | 0.016 | 0.500 |
|  | wt/wt % (%) | 16.75 | 25.00 | 20.00 | 10.00 | 25.00 | 3.25 | 100 |
| Example 3.4 | Mass (g) | 0.084 | 0.125 | 0.025 | 0.160 | 0.096 | 0.010 | 0.500 |
|  | wt/wt % (%) | 16.75 | 25.00 | 5.00 | 32.00 | 19.25 | 2.00 | 100 |

G. Apparatus

Figure 7:
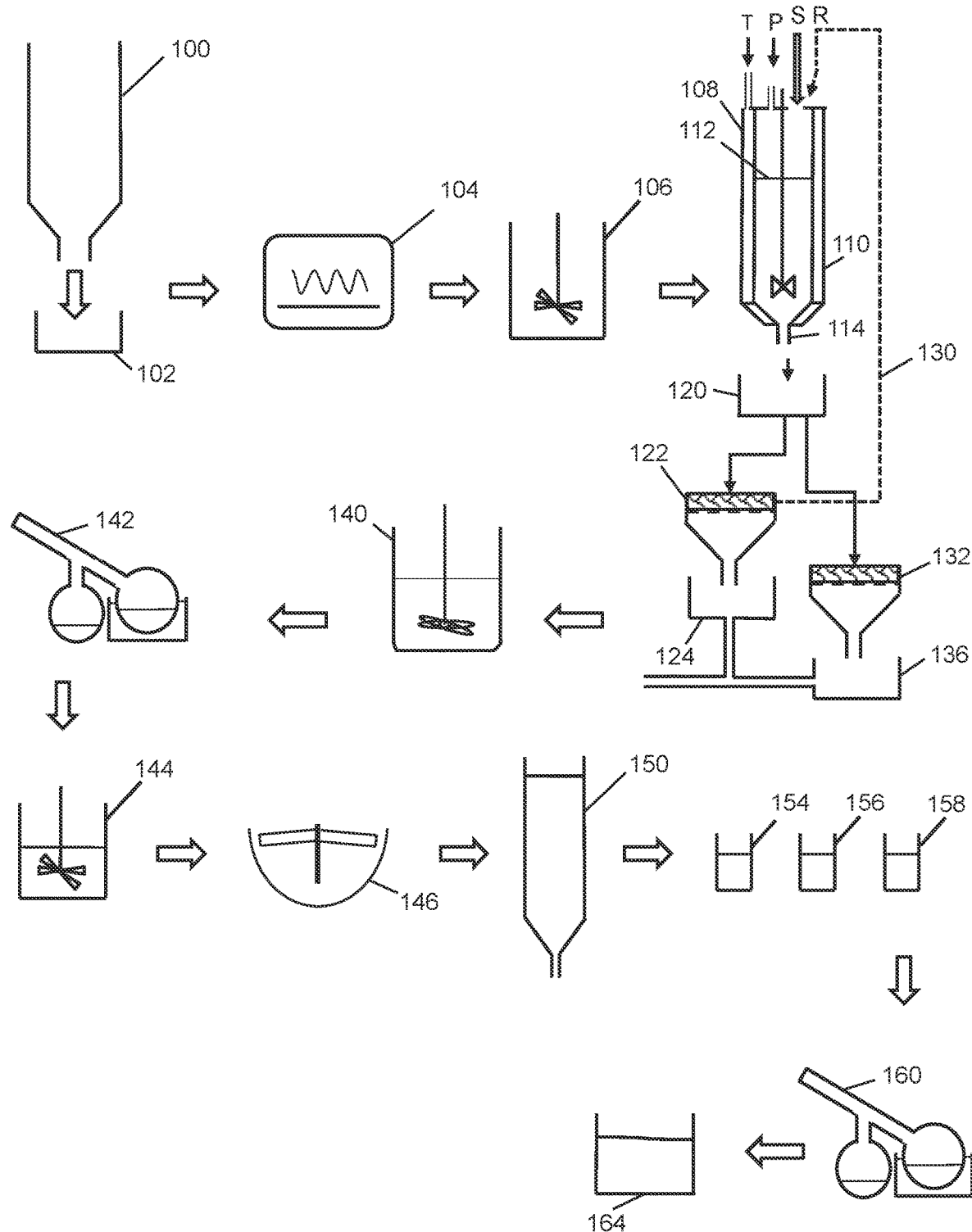
FIG. 7 illustrates a schematic diagram of the apparatus used for obtaining a psychoactive alkaloid extract and a purified psychoactive alkaloid extract.

In one embodiment, FIG. 7 depicts an apparatus used for obtaining a psychoactive alkaloid extract. Raw *Psilocybe cubensis* mushrooms were added to a hopper 100 and were released in batches into container 102. The raw fungal material was then dried in a forced air oven 104 to result in the dried biomass. The dried biomass was placed into a grinder 106 for grinding to result in dried powdered biomass.

The dried powdered biomass was placed into a heat-controlled vessel 110 and acidified solvent (S) was added to the heat-controlled vessel to obtain a specific pH (lower than 3.5). The vessel 110 was surrounded by an insulating wall 108. Alternately, an insulating jacket may have been wrapped around the vessel. The insulating wall 108 or jacket helps to maintain the contents 112 under a constant temperature (T) between 5-95° C. The pressure (P) inside the extraction vessel 110 may be regulated up to from 7 to 20,000 psi. The extraction was performed with a solvent to solid (dried powdered biomass) proportion in the range of 1 L:1 kg to 50 L:1 kg.

After the extraction, the bottom of the extraction vessel 110 was opened at outlet 114 and the extraction slurry was collected in a container 120. The extraction slurry was then In other embodiments, the resultant slurry was transferred to a container 144, where the pH of the extract was adjusted, followed by centrifugation 146 to remove the solid precipitates.

The resultant supernatant was loaded onto a column 150 of resin. An initial wash was given to the column with a solvent to remove impurities from the resin, and fraction 154 was collected. A second wash was given to the column with another solvent to elute the psychoactive alkaloids from the column and result in fraction 156. A final wash was given to the column with another solvent to wash any impurities from the column, to prepare the column for use again, and the fraction 158 was obtained. The elution fraction 156 with the psychoactive alkaloids was then concentrated in a rotary evaporator 160 to result in the purified psychoactive alkaloid solution. The solvent from the purified psychoactive alkaloid solution was solvent is completely or partially evaporated to result in the psychoactive alkaloid extract 164.

In other embodiments, parts of the apparatus may be reused or duplicated. For example, if desired, the elution fraction 156 may be reloaded into the container 144 for pH adjustment and the steps from thereon can be repeated to allow for further purification of the obtained purified psychoactive alkaloid solution.

Figure 8:
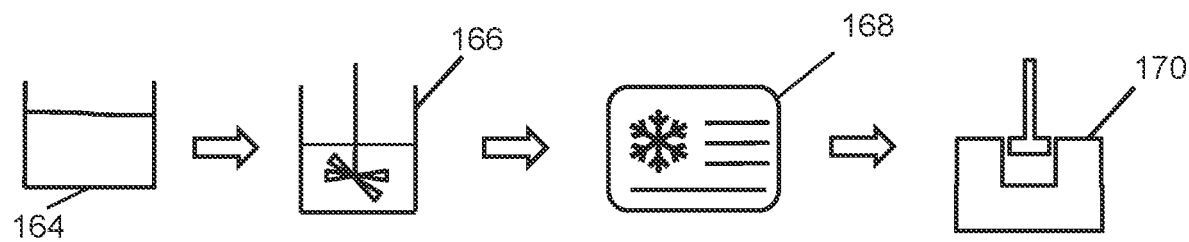
FIG. 8 illustrates a schematic diagram of the apparatus used for obtaining tablets of an oral transmucosal psychoactive alkaloid composition according to an embodiment of the present invention.

In one embodiment, FIG. 8 relates to an apparatus used for obtaining an oral transmucosal psychoactive alkaloid composition. The purified psychoactive alkaloid obtained in container 164 was placed in a beaker 166 along with a mucoadhesive polymer, a carrier and optionally one or more further excipients and mixed thoroughly. This is followed by lyophilization 168 and tablet pressing 170.

Figure 9:
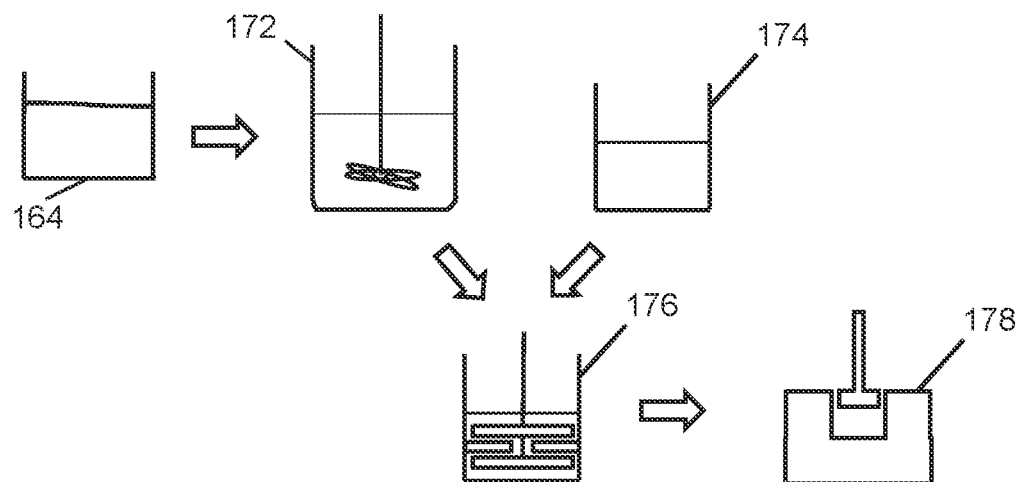
FIG. 9 illustrates a schematic diagram of the apparatus used for obtaining tablets of an oral transmucosal psychoactive alkaloid composition according to an embodiment of the present invention.

In one embodiment, FIG. 9 relates to an apparatus used for obtaining an oral transmucosal psychoactive alkaloid composition. The purified psychoactive alkaloid extract obtained in container 164 was added to container 172, to which was added an appropriate diluent. The carrier and mucoadhesive polymer, along with one or more optional excipients were mixed in a container 174 to result in a dry excipient blend. The mixture from containers 172 and 174 was then combined either via direct pouring or by spraying the liquid onto the dry blend of the excipients in container 176 to obtain a wet mixture, which was mixed by shear mixing. This was followed by tablet pressing 178.

H. Conclusion

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. Steps in the flowchart may be performed in a different order, other steps may be added, or one or more may be removed without altering the main outcome of the processes. In some embodiments, the extract may be replaced with a synthetic psychoactive alkaloid source or composition. The process may be scaled up using larger quantities and a modified apparatus.

All parameters, dimensions, materials, quantities and configurations described herein are examples only and may be changed depending on the specific embodiment. Numbers are given to the nearest significant figure, or to 10%, whichever is the greater. Accordingly, the scope of the invention is to be construed in accordance with the substance defined by the claims.

The invention claimed is:

1. A powdered psychoactive alkaloid composition consisting essentially of, by weight:
   0.1-90% of a psychoactive alkaloid extract from plant material, fungal material or both plant material and fungal material, wherein the psychoactive alkaloid extract comprises psychoactive alkaloid in a concentration of 0.1% to 99% by weight of the psychoactive alkaloid extract, the psychoactive alkaloid being any selection from the group consisting of psilocybin, psilocin, baeocystin, norbaeocystin, norpsilocin, aeruginascin, bufotenin, bufotenidine, 5-methoxy-N,N-Dimethyltryptamine (5-MeO-DMT), N,N-Dimethyltryptamine (DMT), ergine (LSA), ergonovine, ergometrine, muscimol, ibotenic acid, lysergic acid hydroxyethylamide (LSH), elymoclavine, ergometrinine and chanoclavine, wherein the psychoactive alkaloid extract comprises naturally occurring substances selected from the group consisting of fats, sugars, carbohydrates, chitin, chitosan, minerals, waxes and proteins;
   a preservative from over 0% up to 10%, a flow agent from over 0% up to 2%, or both the preservative from over 0% up to 10% and the flow agent from over 0% up to 2%; and
   10-94% of a carrier;
   wherein a concentration of the psychoactive alkaloid in the composition is over 0% and below exactly 10.5%.

2. The composition of claim 1, comprising 2-90% of the psychoactive alkaloid extract.

3. The composition of claim 1, wherein the preservative is selected from the group consisting of ascorbic acid, citric acid, lactose, vitamin A, vitamin E, retinyl palmitate, selenium, sodium citrate, sodium ascorbate, calcium ascorbate, sodium benzoate and potassium benzoate.

4. The composition of claim 1, wherein the flow agent is selected from the group consisting of silicon dioxide, stearic acid, magnesium stearate and talc.

5. The composition of claim 1, wherein the concentration of the psychoactive alkaloid in the composition is defined as a percentage with a precision of two decimal places.

6. The composition of claim 1, wherein the concentration of the psychoactive alkaloid in the psychoactive alkaloid extract is from 0.1% to 10% by weight.

7. The composition of claim 1, wherein the psychoactive alkaloid extract is a purified psychoactive alkaloid extract, and the concentration of the psychoactive alkaloid in the psychoactive alkaloid extract is from 10% to 99% by weight.

8. The composition of claim 1, comprising 0.1-79.6% of the psychoactive alkaloid extract.

9. The composition of claim 1, wherein the concentration of the psychoactive alkaloid in the psychoactive alkaloid extract is 0.1-75.22% by weight.

10. The composition of claim 1, wherein the naturally occurring substances are present in the psychoactive alkaloid extract in a concentration ranging from 1%-99.9% by weight.

11. The composition of claim 1, wherein the psychoactive alkaloid extract is from fungi.

12. The composition of claim 11, wherein the psychoactive alkaloid extract is from *Psilocybe cyanescens, Psilocybe cubensis, Amanita muscaria*, or any selection therefrom.

13. The composition of claim 1, wherein the psychoactive alkaloid extract is from psychoactive plants.

14. The composition of claim 13, wherein the psychoactive alkaloid extract is from *Anadenanthera colubrina*.

15. The composition of claim 13, wherein the psychoactive alkaloid extract is from *Anadenanthera peregrina*.

16. The composition of claim 1, wherein the carrier is selected from the group consisting of starch, maltodextrin, tapioca maltodextrin, rice maltodextrin, alpha cyclodextrin, beta cyclodextrin, microcrystalline cellulose, gum arabic, xanthan gum, guar gum and cellulose gum.

17. The composition of claim 1, wherein a total amount of the preservative, the flow agent and the carrier is selected so that the concentration of the psychoactive alkaloid in the composition is a desired specific amount defined to two significant figures.

18. The composition of claim 1, wherein a total amount of the preservative, the flow agent and the carrier is selected so that the concentration of the psychoactive alkaloid in the composition is a desired specific amount defined to three significant figures.

19. The composition of claim 1, wherein a total amount of the preservative, the flow agent and the carrier is selected so that the concentration of the psychoactive alkaloid in the composition is a desired specific amount defined to four significant figures.

20. The composition of claim 1, wherein the concentration of the psychoactive alkaloid in the composition is over 0.50% and below exactly 10.5%.

21. A powdered psychoactive alkaloid composition consisting essentially of, by weight:
- 0.1-90% of a psychoactive alkaloid extract from plant material, fungal material or both plant material and fungal material, wherein the psychoactive alkaloid extract comprises psychoactive alkaloid in a concentration of 0.1% to 99% by weight of the psychoactive alkaloid extract, the psychoactive alkaloid being any selection from the group consisting of psilocybin, psilocin, baeocystin, norbaeocystin, norpsilocin, aeruginascin, bufotenin, bufotenidine, 5-methoxy-N,N-Dimethyltryptamine (5-MeO-DMT), N,N-Dimethyltryptamine (DMT), ergine (LSA), ergonovine, ergometrine, muscimol, ibotenic acid, lysergic acid hydroxyethylamide (LSH), elymoclavine, ergometrinine and chanoclavine, wherein the psychoactive alkaloid extract comprises naturally occurring substances selected from the group consisting of fats, sugars, carbohydrates, chitin, chitosan, minerals, waxes and proteins;
- a preservative from over 0% up to 10%, a flow agent from over 0% up to 2%, or both the preservative from over 0% up to 10% and the flow agent from over 0% up to 2%;
- an antioxidant from over 0% up to 0.5%; and
- 10-94% of a carrier;
- wherein a concentration of the psychoactive alkaloid in the composition is over 0% and below exactly 10.5%.

22. The composition of claim 21, wherein a total amount of the preservative, the flow agent, the antioxidant, and the carrier are selected so that the concentration of the psychoactive alkaloid in the composition is a desired specific amount defined to two significant figures.

23. The composition of claim 21, wherein a total amount of the preservative, the flow agent, the antioxidant, and the carrier are selected so that the concentration of the psychoactive alkaloid in the composition is a desired specific amount defined to three significant figures.

24. The composition of claim 21, wherein a total amount of the preservative, the flow agent, the antioxidant, and the carrier are selected so that the concentration of the psychoactive alkaloid in the composition is a desired specific amount defined to four significant figures.

25. The composition of claim 21, wherein the concentration of the psychoactive alkaloid in the composition is over 0.50% and below exactly 10.5%.

26. A powdered psychoactive alkaloid composition consisting essentially of, by weight:
- 0.1-90% of a psychoactive alkaloid extract from plant material, fungal material or both plant material and fungal material, wherein the psychoactive alkaloid extract comprises psychoactive alkaloid in a concentration of 0.1% to 99% by weight of the psychoactive alkaloid extract, the psychoactive alkaloid being any selection from the group consisting of psilocybin, psilocin, baeocystin, norbaeocystin, norpsilocin, aeruginascin, bufotenin, bufotenidine, 5-methoxy-N,N-Dimethyltryptamine (5-MeO-DMT), N,N-Dimethyltryptamine (DMT), ergine (LSA), ergonovine, ergometrine, muscimol, ibotenic acid, lysergic acid hydroxyethylamide (LSH), elymoclavine, ergometrinine and chanoclavine, wherein the psychoactive alkaloid extract comprises naturally occurring substances selected from the group consisting of fats, sugars, carbohydrates, chitin, chitosan, minerals, waxes and proteins;
- a preservative from over 0% up to 10%, a flow agent from over 0% up to 2%, or both the preservative from over 0% up to 10% and the flow agent from over 0% up to 2%; a bioavailability agent from over 0% up to 0.5%; and
- 10-94% of a carrier; wherein a concentration of the psychoactive alkaloid in the composition is over 0% and below exactly 10.5%.

27. The composition of claim 26, wherein a total amount of the preservative, the flow agent, the bioavailability agent, and the carrier are selected so that the concentration of the psychoactive alkaloid in the composition is a desired specific amount defined to two significant figures.

28. The composition of claim 26, wherein a total amount of the preservative, the flow agent, the bioavailability agent, and the carrier are selected so that the concentration of the psychoactive alkaloid in the composition is a desired specific amount defined to three significant figures.

29. The composition of claim 26, wherein a total amount of the preservative, the flow agent, the bioavailability agent, and the carrier are selected so that the concentration of the psychoactive alkaloid in the composition is a desired specific amount defined to four significant figures.

30. The composition of claim 26, wherein the concentration of the psychoactive alkaloid in the composition is over 0.50% and below exactly 10.5%.

* * * * *